(12) United States Patent
Niemczak et al.

(10) Patent No.: US 8,109,008 B1
(45) Date of Patent: Feb. 7, 2012

(54) DIGITAL HEIGHT ROD

(75) Inventors: Stephen Niemczak, Mokena, IL (US); Jerome Montgomery, Jr., Dolton, IL (US); Anthony Harvey, Dolton, IL (US); Harrison Yuan, Buffalo Grove, IL (US)

(73) Assignee: Pelstar, LLC, Alsip, IL (US)

( * ) Notice: Subject to any disclaimer, the term of this patent is extended or adjusted under 35 U.S.C. 154(b) by 0 days.

(21) Appl. No.: 12/942,894

(22) Filed: Nov. 9, 2010

(51) Int. Cl.
*A61B 5/107* (2006.01)

(52) U.S. Cl. .............................. 33/832; 33/512; 600/587

(58) Field of Classification Search .................... 33/512, 33/706, 832; 600/587
See application file for complete search history.

(56) References Cited

U.S. PATENT DOCUMENTS

| | | | |
|---|---|---|---|
| 3,616,690 A | 11/1971 | Harden | |
| 3,676,934 A | 7/1972 | Freer | |
| 3,724,574 A | 4/1973 | Hutchinson et al. | |
| 3,808,694 A | 5/1974 | Hutchinson et al. | |
| 4,037,325 A | 7/1977 | Weber et al. | |
| 4,187,612 A | 2/1980 | Scott | |
| 4,336,855 A | 6/1982 | Chen | |
| 4,518,052 A | 5/1985 | Chen | |
| 4,679,326 A | 7/1987 | Takizawa et al. | |
| 4,923,024 A | 5/1990 | Ferrer et al. | |
| 4,939,849 A * | 7/1990 | Johnson | 33/512 |
| 5,174,402 A | 12/1992 | Chen | |
| 5,379,028 A | 1/1995 | Chung | |
| 5,415,176 A | 5/1995 | Sato et al. | |
| 5,611,351 A | 3/1997 | Sato et al. | |
| 6,327,494 B1 | 12/2001 | Sakai | |
| 6,539,310 B2 | 3/2003 | Shimomura | |
| 6,847,586 B1 | 1/2005 | Chen | |
| 6,982,929 B2 | 1/2006 | Moss et al. | |
| 7,163,516 B1 | 1/2007 | Pagnacco et al. | |
| 7,170,016 B2 | 1/2007 | Dumornay et al. | |
| 7,181,861 B1 * | 2/2007 | Leser | 33/832 |
| 7,200,952 B2 | 4/2007 | Montagnino | |
| D592,535 S | 5/2009 | Li et al. | |
| 7,765,711 B2 * | 8/2010 | Schneeberger et al. | 33/706 |
| 2004/0107593 A1 * | 6/2004 | Rego | 33/512 |
| 2005/0155246 A1 * | 7/2005 | Montagnino | 33/832 |
| 2006/0191154 A1 * | 8/2006 | Kraemer | 33/832 |
| 2011/0167658 A1 * | 7/2011 | Chul | 33/512 |

OTHER PUBLICATIONS

Seca, Digital weighing and measuring station with automatic BMI calculation, accessed Nov. 9, 2009 (2 pages).
Tanita, TBF-215GS Body Composition Analyzer, <https://www.tanita.com/en/tbf-215gs/184-catld.520093719.html> accessed Nov. 9, 2009 (2 pages).
Shekel, H121-00-4 Digital Ultrasonic Measure Device & Physician Scales, <http://healthcarescales.com/page.aspx?page_id=86>, accessed Nov. 9, 2009 (2 pages).

(Continued)

*Primary Examiner* — G. Bradley Bennett
(74) *Attorney, Agent, or Firm* — Michael Best & Friedrich LLP

(57) ABSTRACT

A device and method for determining the length of an object. The device includes a height rod assembly with a uniform marker row and a non-uniform marker row detected by sensors to determine the location of the height rod assembly which is translated to the height or length of the measured object. The uniform marker row includes uniform markers of equal length spaced apart by a uniform length. The non-uniform marker row is divided into equal sections, each section including a non-uniform marker with a unique length adjacent to a non-uniform spacing with a unique length. Upon startup, a controller determines the location of the height rod assembly within a set distance of movement regardless of the position of the height rod assembly. The height rod assembly is telescoping rod assembly including sensors, uniform marker row, and non-uniform marker row for each height rod section.

25 Claims, 22 Drawing Sheets

OTHER PUBLICATIONS

Detecto, DLM Digital Baby Length Measuring Device, <http://www.detecto.com/DLM.htm>, accessed Nov. 9, 2009 (1 page).
Detecto, 6854 Bariatric Scale with Digital Height Rod, <http://www.detecto.com/6854DHR.htm>, accessed Nov. 9, 2009 (1 page).
Detecto, 6857DHR Bariatric Scale with Digital Height Rod, <http://www.detecto.com/6857DHR.htm>, accessed Nov. 9, 2009 (1 page).
Seca, 242-Electronic Measuring Rod with Cable-Free Display, <https://www.seca-online.com/seca-242.677.0.html?&L=1&C=us>, accessed Nov. 9, 2009 (1 page).
Detecto, DHRWM Stand-Alone Wall-Mount Digital Height Rods, <http://www.detecto.com/DHRWM.htm>, accessed Nov. 9, 2009 (1 page).
Detecto, PD300DHR ProDoc Professional Doctor Scale, <http://www.detecto.com/PD300DHR.htm>, accessed Nov. 10, 2009 (2 pages).
Detecto, 6437DHR Digital Eye-Level Physician Scale with Digital Height Rod, <http://www.detecto.com/6437DHR.htm> accessed Nov. 10, 2009 (1 page).

* cited by examiner

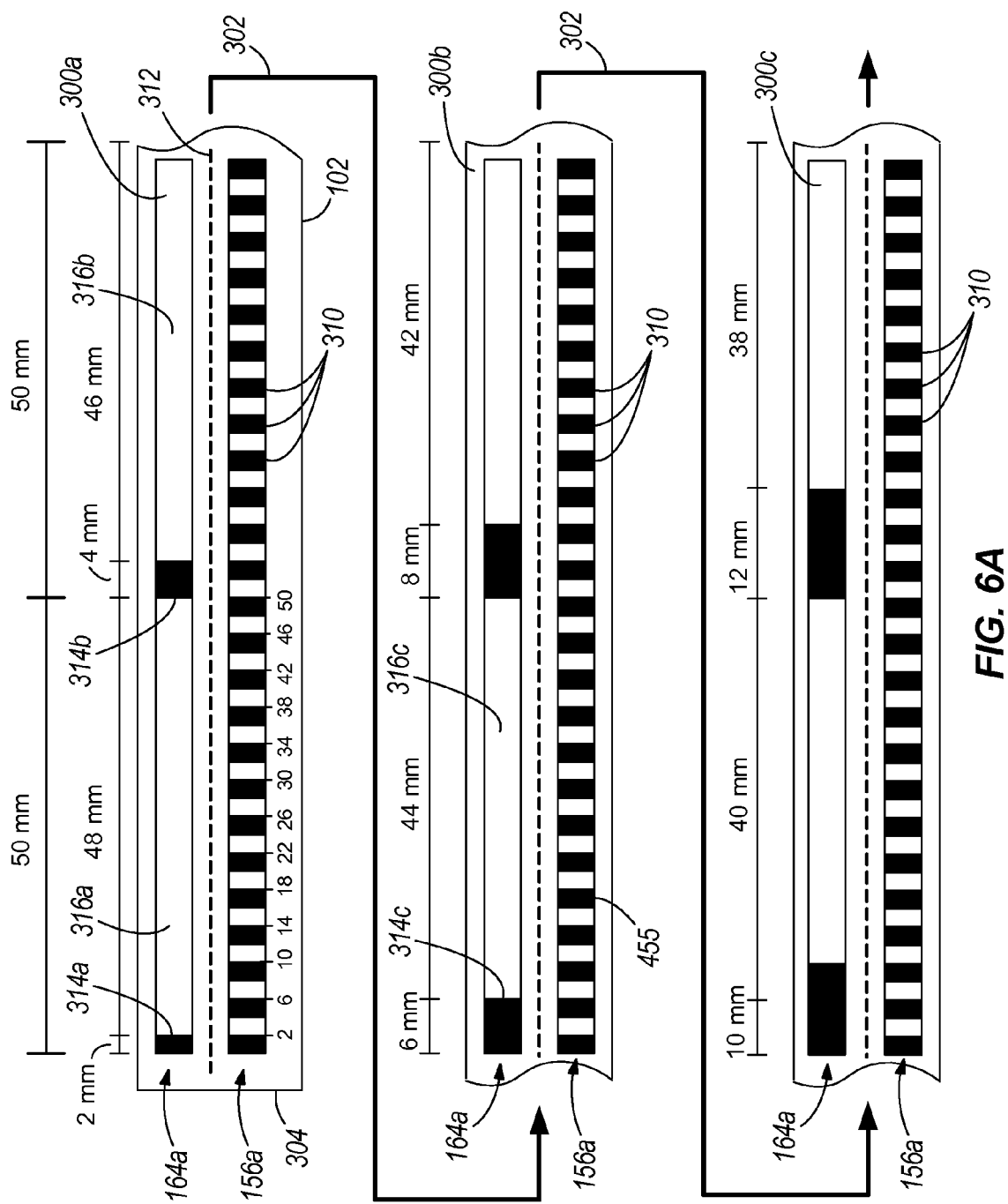

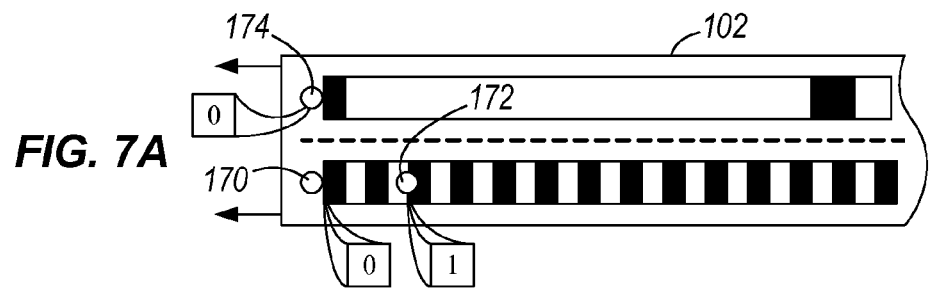
FIG. 7A — State 3
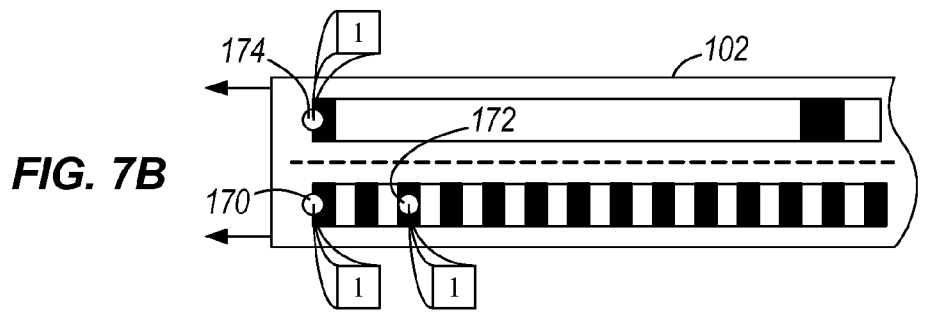
FIG. 7B — State 4
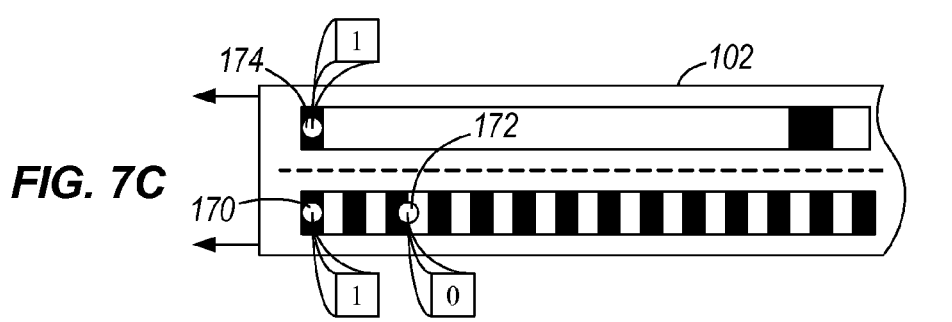
FIG. 7C — State 1
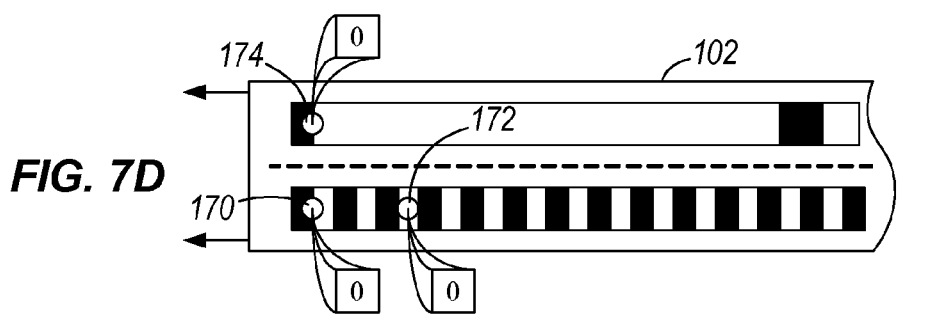
FIG. 7D — State 2
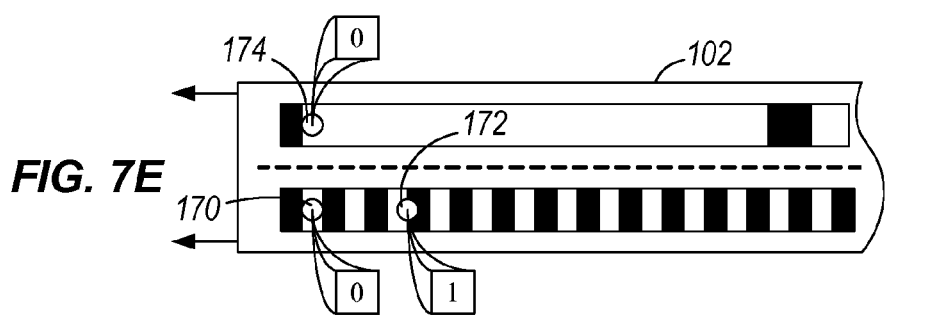
FIG. 7E — State 3

DIGITAL HEIGHT ROD

FIELD OF THE INVENTION

The present invention relates to devices used for measuring the height or length of an object, such as a human, and, more particularly to a height rod.

SUMMARY

In one independent embodiment, a device for measuring the length of an object may generally include a first member; a second member movable relative to the first member; a uniform marking row including uniform markers, each uniform marker having a first length; a non-uniform marking row divided into equal sections, each section including a unique marker and a unique spacing, a length of the unique marker and a length of the unique spacing of each section each uniquely identifying the section; a first sensor positioned to detect the uniform markers as the first member and the second member are relatively moved, the first sensor generating a first output indicative of whether a uniform marker is detected; a second sensor positioned to detect the uniform markers as the first member and the second member are relatively moved, the second sensor generating a second output indicative of whether a uniform marker is detected; an absolute sensor positioned to detect the unique markers and unique spacings as the first member and the second member are relatively moved, the absolute sensor generating an absolute output, the absolute output indicating transitions between the unique markers and unique spacings; and a controller coupled to the first sensor, the second sensor, and the absolute sensor, the controller determining a location of the movable member based the first output, the second output, and the absolute output to thereby determine the length of the object.

In another independent embodiment, a device for detecting a length of an object along an axis may generally include a telescoping rod assembly including a first rod and a second rod extendable along the axis; a first sensor board operable to detect markings on the first rod and output first length data; a second sensor board operable to detect markings on the second rod and output second length data, the second sensor board being spaced from the first sensor board along the axis; and a controller coupled to the first sensor board and to the second sensor board, the controller being operable to receive the first length data and the second length data, determine the length of the object using the first length data when the telescoping rod assembly is positioned below a predetermined level, and determine the length of the object using the second length data when the telescoping rod assembly is positioned above the predetermined level.

In yet another independent embodiment, a method of determining a length of an object may generally include moving a first member relative to a second member; receiving a first output from an absolute sensor indicating that the absolute sensor has transitioned between a marker and a spacing of a non-uniform marking row, the non-uniform marking row being divided into equal sections, each section including a unique marker and a unique spacing, a length of the unique marker and a length of the unique spacing of each section uniquely identifying the section; receiving movement data from a first sensor and a second sensor indicating a direction and distance of relative movement of the first member and the second member since the transition of the absolute sensor; receiving a second output from the absolute sensor indicating a subsequent transition of the absolute sensor from one of the marker and the spacing to one of a second spacing and a second marker; identifying one of the marker and the spacing based on the first output, the second output, and the movement data; and determining a location of the first member relative to the second member based on the identification of one of the marker and the spacing.

In independent embodiments, a digital height rod assembly may be used for measuring the height or length of an object. The digital height rod assembly may include a uniform marker row and a non-uniform marker row detected by sensors to determine the location of the height rod. The location of the height rod assembly is translated to the height or length of the measured object. The uniform marker row includes uniform markers of equal length spaced apart by a uniform length. The non-uniform marker row is divided into equal sections, each section including a non-uniform marker with a unique length adjacent to a non-uniform spacing with a unique length. Upon startup, the digital height rod is operable to determine its location within a set distance of movement regardless of the position of the height rod.

In independent embodiments a telescoping height rod assembly may include a first rod and a second rod each associated with a sensor board, a uniform marker row, and a non-uniform marker row. When the telescoping height rod assembly is below a predetermined level, the first rod and its associated sensor board, uniform marker row, and non-uniform marker row are used to determine the location of the telescoping height rod assembly. When the telescoping height rod is above a predetermined level, the second rod and its associated sensor board, uniform marker row, and non-uniform marker row are used to determine the location of the telescoping height rod assembly. Additionally, the first rod and second rod interlock for integral movement after (e.g., above) the predetermined level but disengage for independent movement of the first rod when before (e.g., below) the predetermined level.

Independent aspects of the invention will become apparent by consideration of the detailed description, claims and accompanying drawings.

BRIEF DESCRIPTION OF THE DRAWINGS

FIGS. 6A-6B illustrate several portions of the height rod assembly including uniform and non-uniform markers.

FIGS. 7A-7E illustrate movement of a portion of the height rod assembly relative to sensors and resulting sensor output values.

DETAILED DESCRIPTION

Before any independent embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
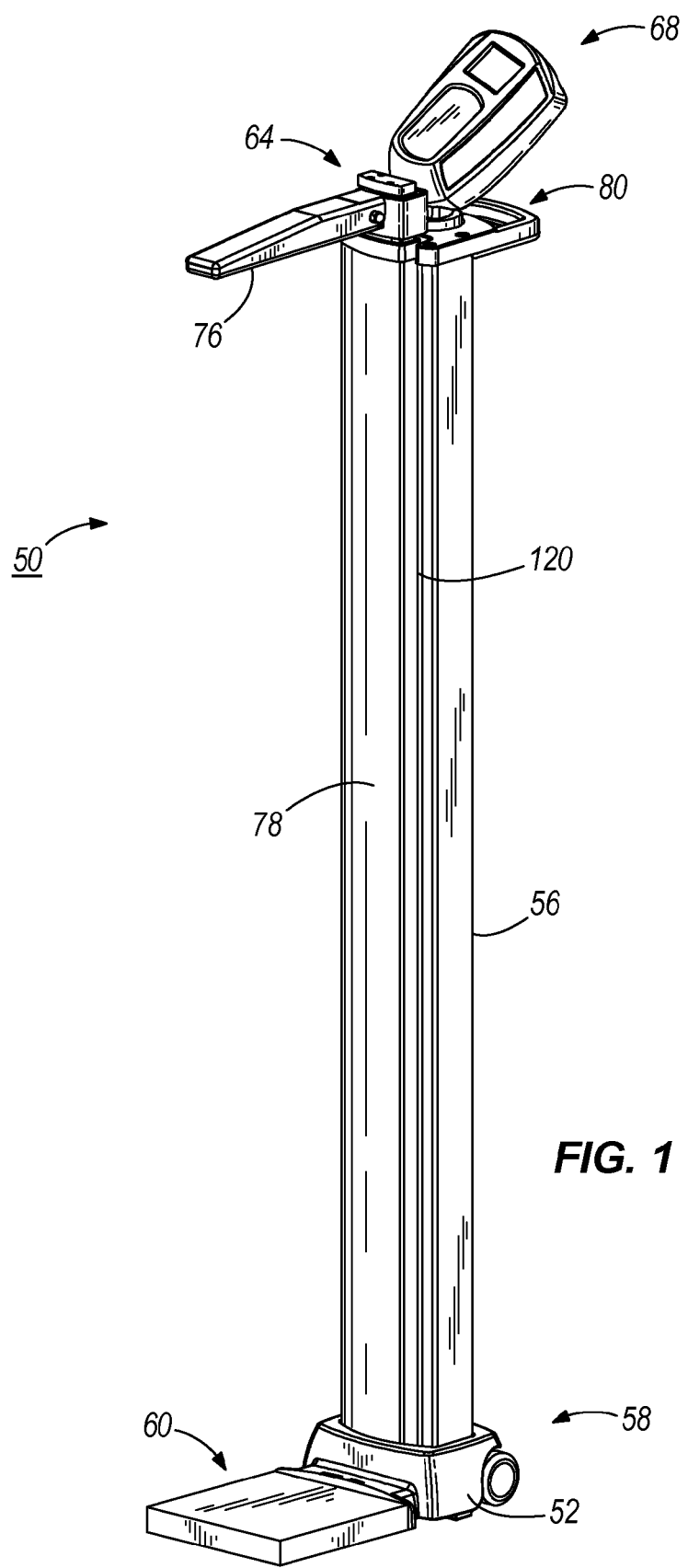
FIG. 1 illustrates a scale that measures and displays the height and weight of an object.

FIG. 1 illustrates a measuring device, such as a scale 50, that measures and displays the height and/or weight of an object (e.g., a patient). The scale 50 generally includes a base 52 and a pillar 56, cooperating to provide a frame assembly 58, a weight measurement device 60, a height rod assembly 64 and a head or display 68 for displaying information and/or receiving user input. The weight measurement device 60 is supported by the frame assembly 58 and is operable to detect the weight of an object (e.g., the patient) positioned thereon. The weight measurement device 60 outputs an indication of the detected weight to the display 68. Components of the scale 50, such as, for example, the weight measurement device 60, may be similar to the components illustrated and described in U.S. Pat. No. 7,550,682, issued Jun. 23, 2009, the entire contents of which are hereby incorporated by reference.

Figure 2A:
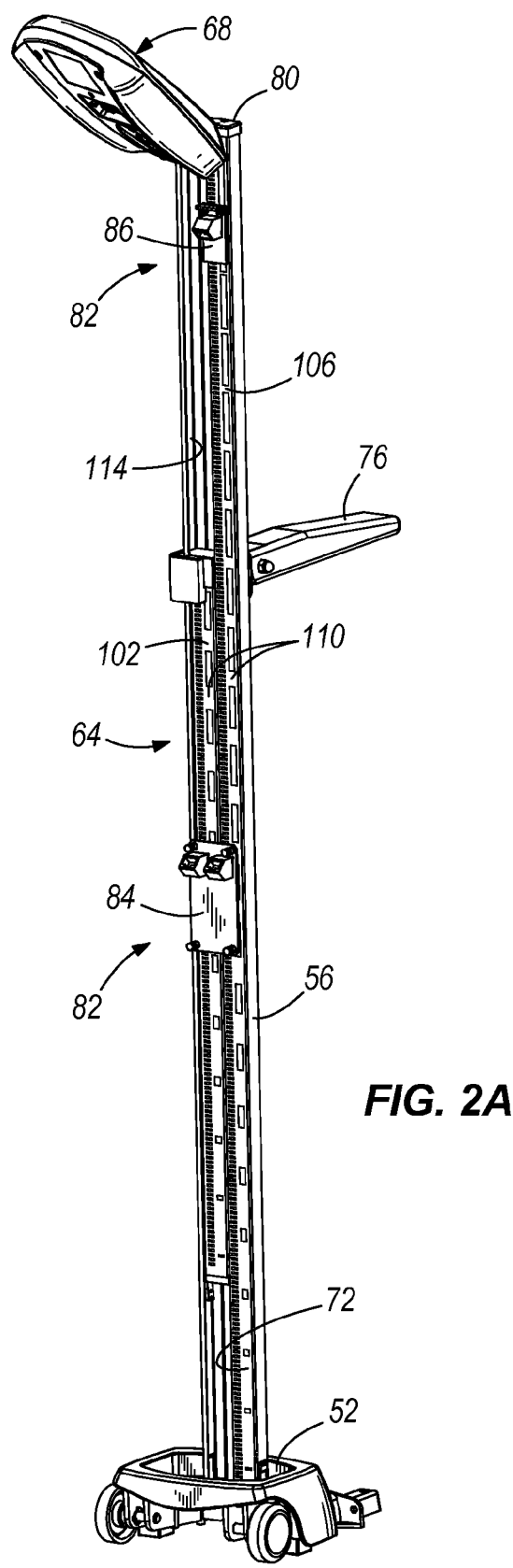
FIGS. 2A-2C illustrate a height rod assembly extended and retracted to various heights.
Figure 2B:
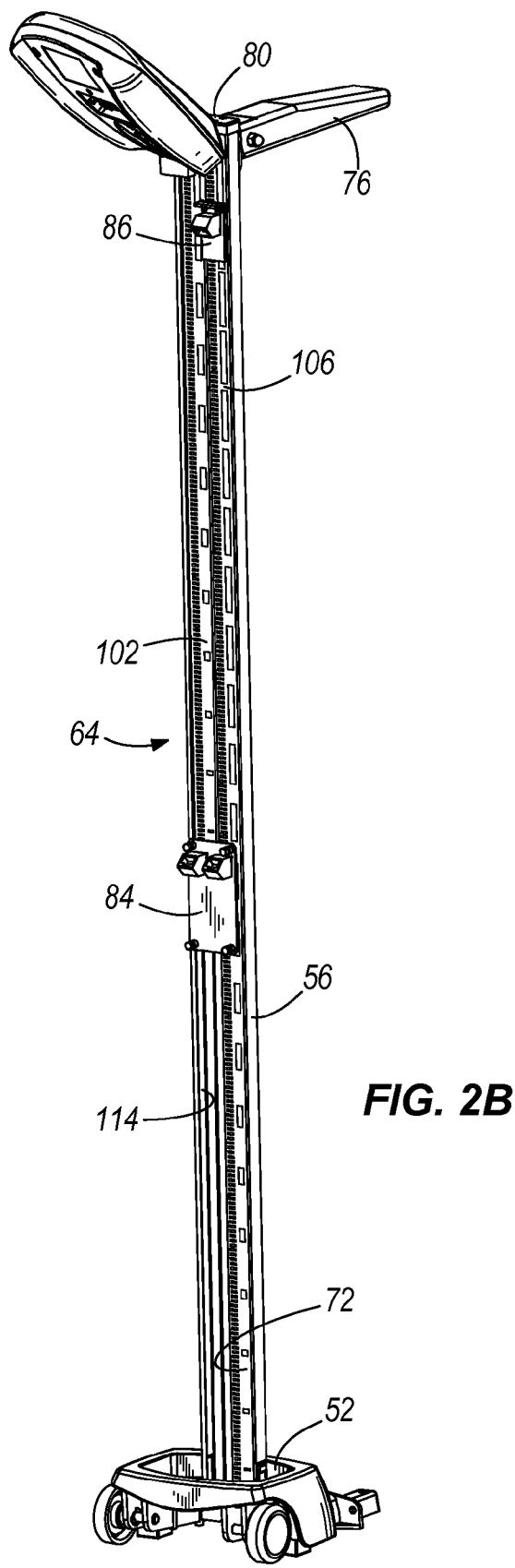
Figure 2C:
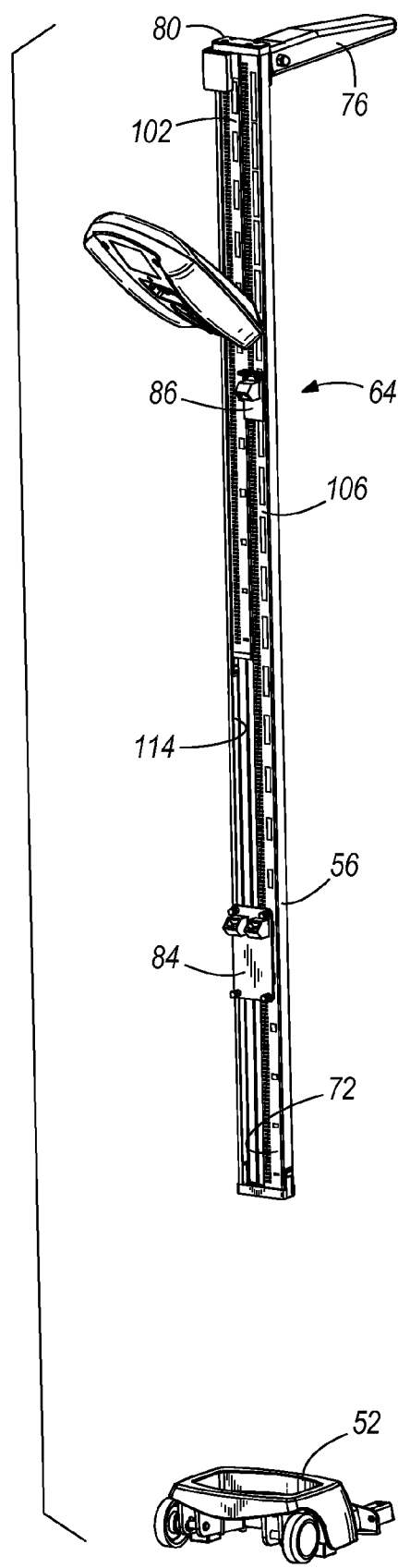

The height rod assembly 64 is generally a telescoping rod assembly that moves up and down along a track 72 (see FIGS. 2A-2C and 3-4) within the pillar 56. In use, an arm 76 is connected to the end of the height rod assembly 64, and the height rod assembly 64 is adjusted to raise or lower until the arm 76 to rest on a patient's head. FIGS. 2A-2C illustrate the scale 50 with the height rod assembly 64 in various height positions (with the pillar cover 78 removed). In FIG. 2A, the height rod assembly 64 is positioned with the arm 76 at a first (retracted) position below the top 80 of the pillar 56. In FIG. 2B, the height rod assembly 64 is positioned with the arm 76 at a second (intermediate) position approximately even with the top 80 of the pillar 56. In FIG. 2C, the height rod assembly 64 is positioned with the arm 76 at a third (extended) position above the top 80 of the pillar 56

A sensor arrangement 82 (see FIGS. 2A-2C and 3-4) determines the position of the height rod assembly 64 (e.g., the extent to which the height rod assembly 64 is extended or retracted) and thereby the height of the patient, and output the determined position/height to the display 68. As shown in FIGS. 2A-2C, in the illustrated construction, the sensor arrangement 82 includes a lower sensor board 84 and an upper sensor board 86 supported on the pillar 56. The upper sensor board 86 includes a connector 90 (see FIG. 4) coupled to a connector 92 (see FIG. 3) of the lower sensor board 84. The lower sensor board 84 is coupled via connector 94 (see FIG. 3) to a connector (not shown) of display 68.

A controller 98 (see FIG. 5) receives data from the weight measurement device 60 and from the sensor arrangement 82 (see FIGS. 2A-2C) for the height rod assembly 64. The controller 98 interprets the received information as a weight and a height and displays the weight and the height on the display 68 for the user to view.

In the illustrated construction (see FIGS. 2A-2C and 3-4), the telescoping height rod assembly 64 is a two-piece assembly including an inner rod 102 and an outer rod 106. The illustrated rods 102 and 106 each have a generally flat face 110 (see FIG. 2A) and an opposite rounded face (not shown), and the inner rod 102 is shorter than the outer rod 106. In some constructions, the inner rod 102 may be the same length as or longer than the outer rod 106.

The rods 102 and 106 are operable to slide up and down along the pillar 56. The inner rod 102 slides along a track 114 defined by the outer rod 106, and the outer rod 106 slides along the track 72 defined by the pillar 56. In the illustrated construction, the height rod assembly 64 is operable to measure heights between two feet, five inches and seven feet, four inches but may be operable in other constructions to measure heights in different ranges.

Figure 4:
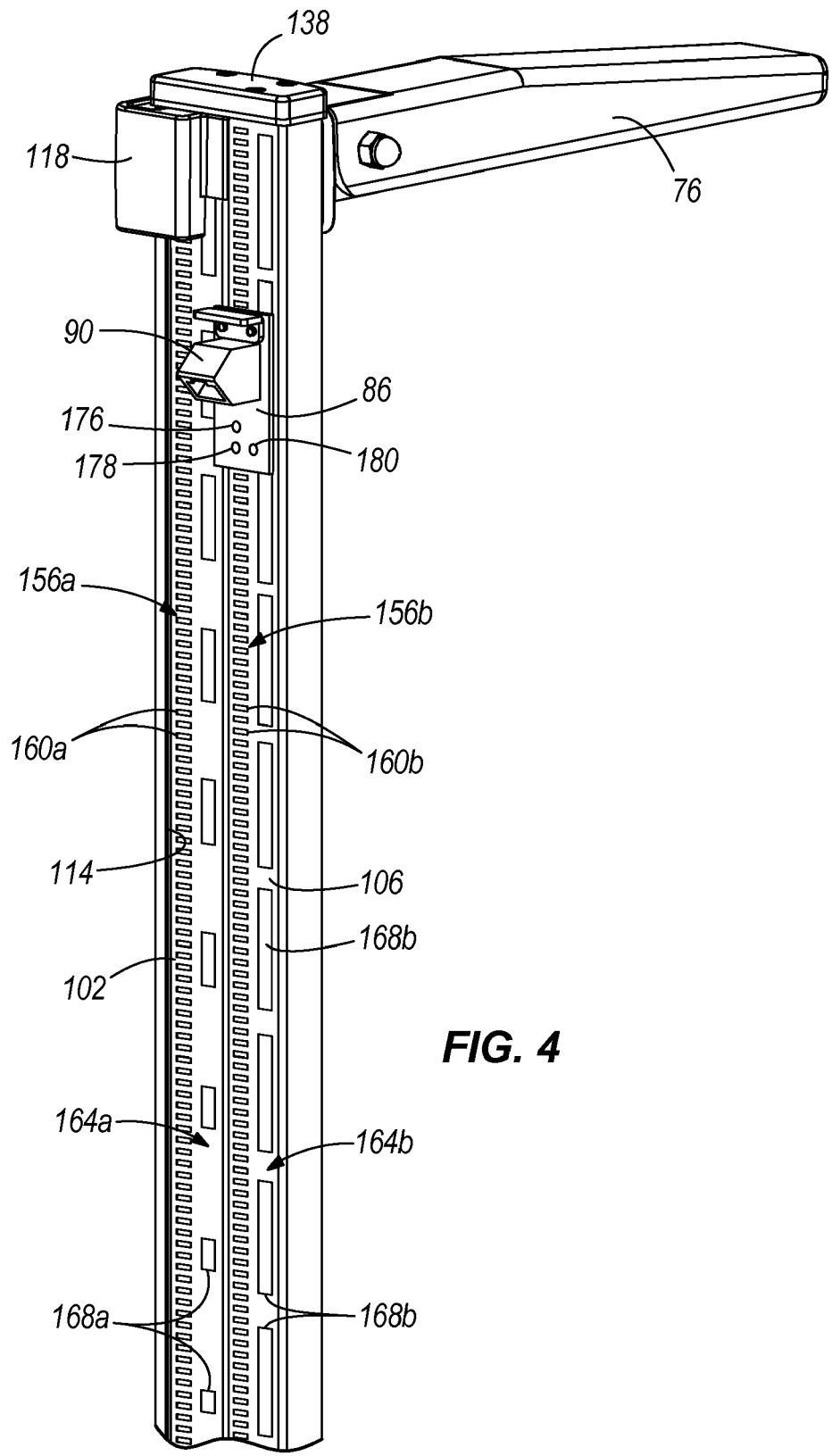
FIG. 4 illustrates an upper sensor board, a portion of the height rod assembly and an arm of the scale.

The arm 76 is coupled to a top portion of the inner rod 102 with an arm connector 118 (see FIG. 4). The arm 76 and the arm connector 118 move integrally with the inner rod 102 along the track 114 in response to user force (e.g., on the arm 76). As shown in FIG. 1, the pillar cover 78 defines a groove 120 to enable the arm 76, the arm connector 118, and the inner rod 102 slide along the track 114 and below the top 80 of the pillar 56.

In positions in which the arm 76 is positioned below the top 80 of the pillar 56 ("retracted" positions, such as in FIG. 2A), the inner rod 102 (and the arm 76 and the arm connector 118) slide relative to the frame assembly 58 (e.g., relative to the pillar 56), and the outer rod 106 remains stationary. Also, in retracted positions (such as in FIG. 2A), when no user force is present, friction between the inner rod 102 and the track 114 holds the inner rod 102 in position. In positions in which the arm 76 is above the top 80 of the pillar 56 ("extended" positions, such as in FIG. 2C), the rods 102 and 106 (and the arm 76 and the arm connector 118) slide as a unit relative to the pillar 56, and, when no user force is present, friction between the outer rod 106 and the track 72 hold the unit in position.

Figure 2D:
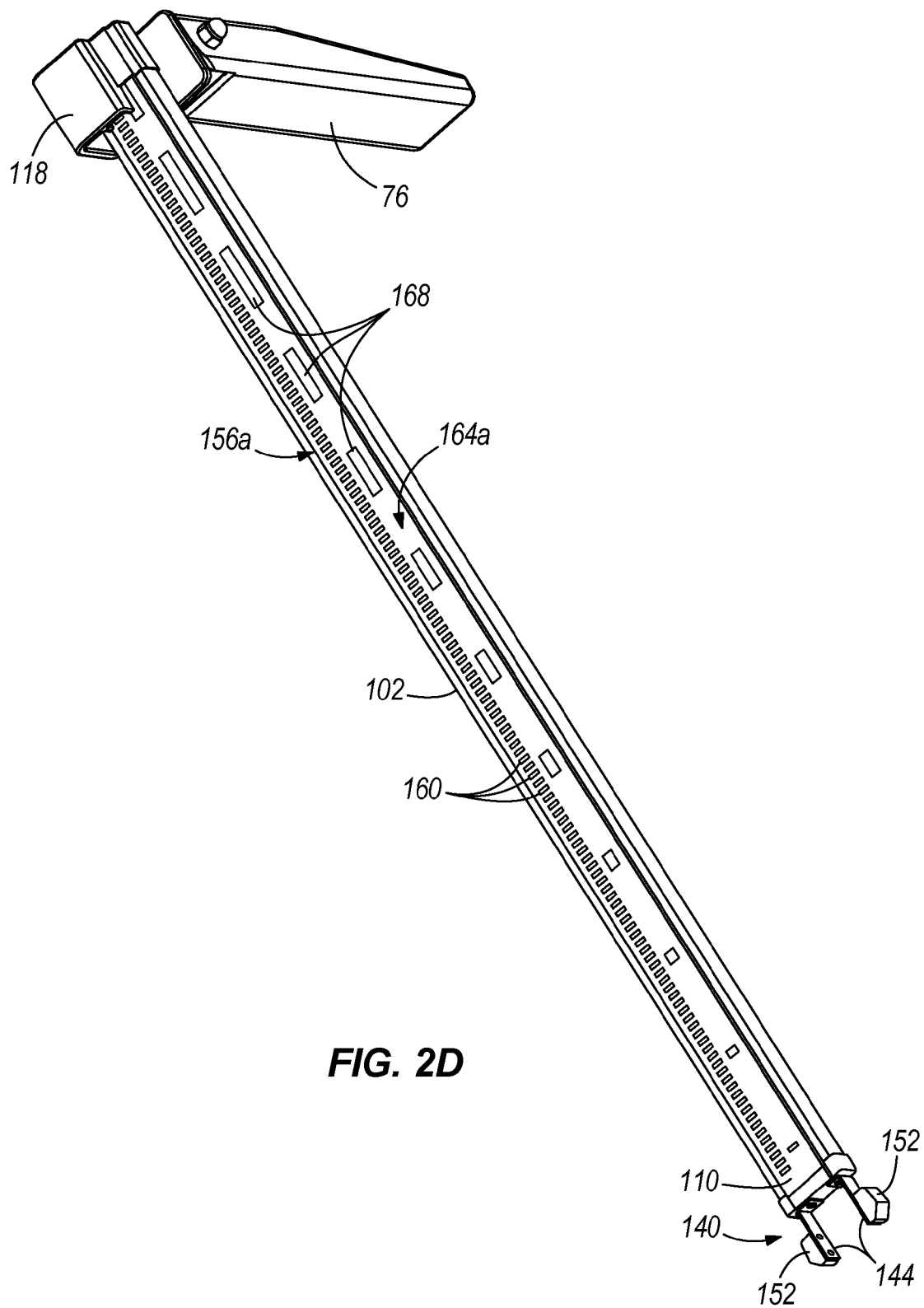
FIGS. 2D-2J illustrate portions of the height rod assembly and locking mechanisms.
Figure 2E:
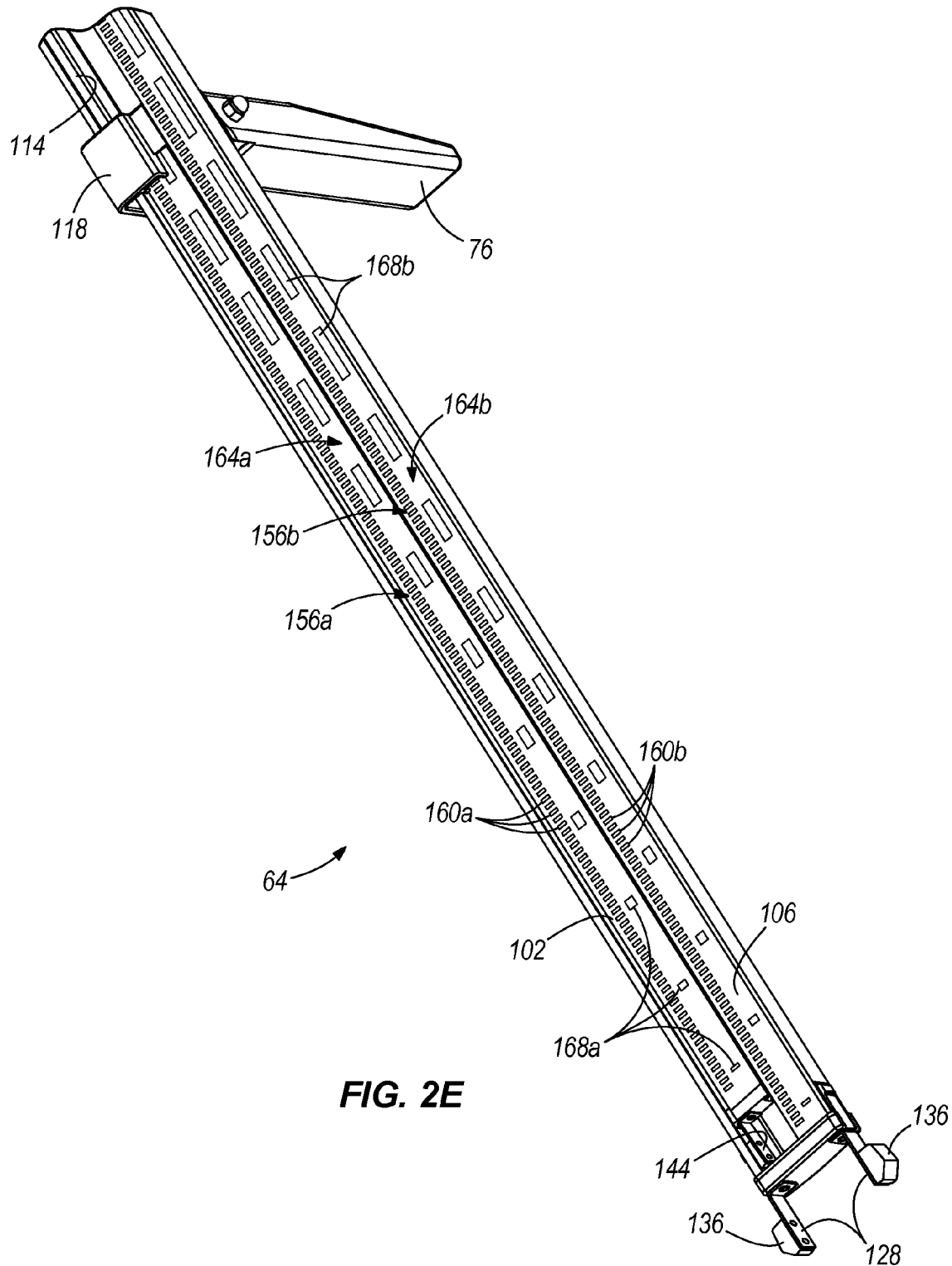
Figure 2F:
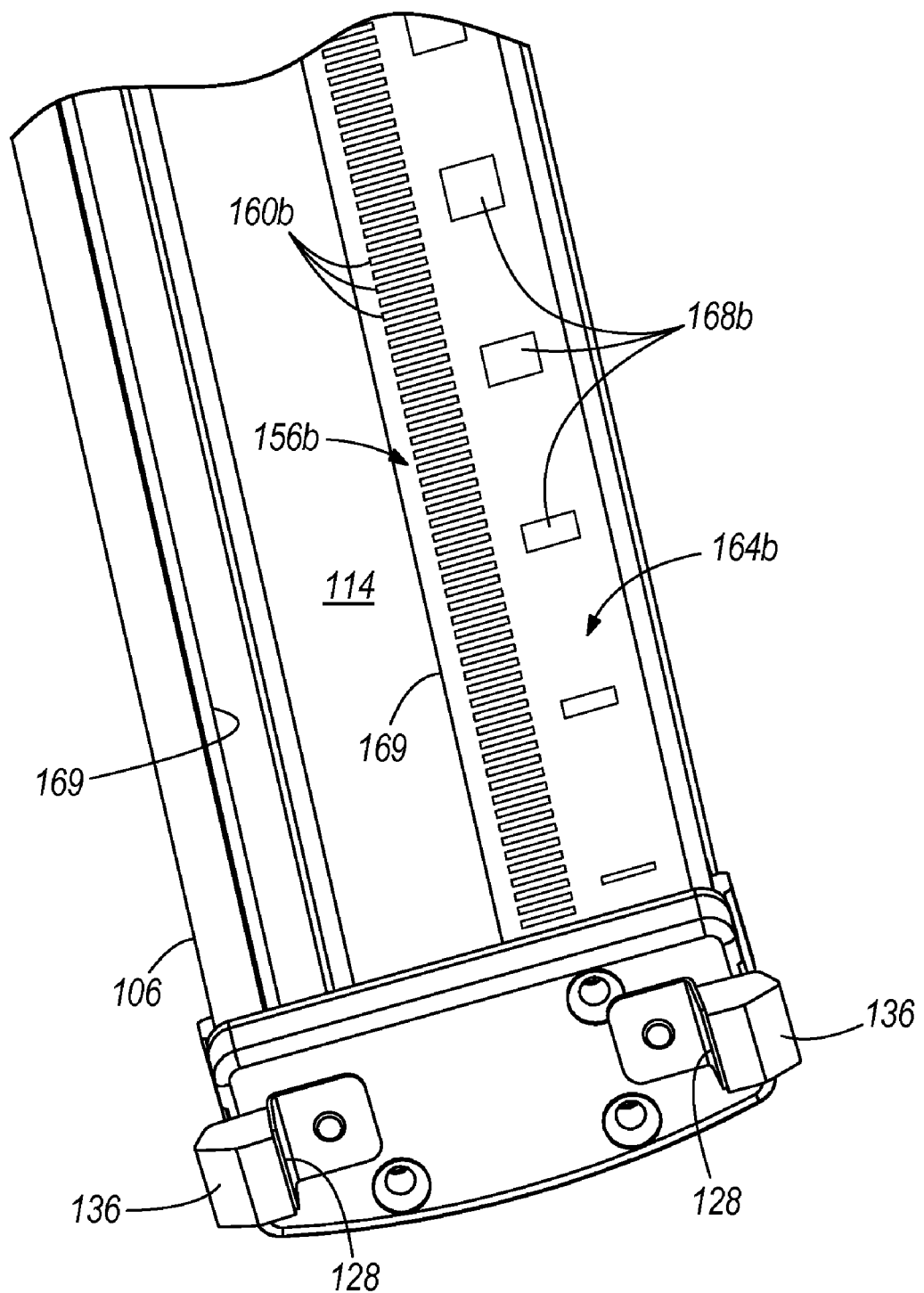
Figure 2G:
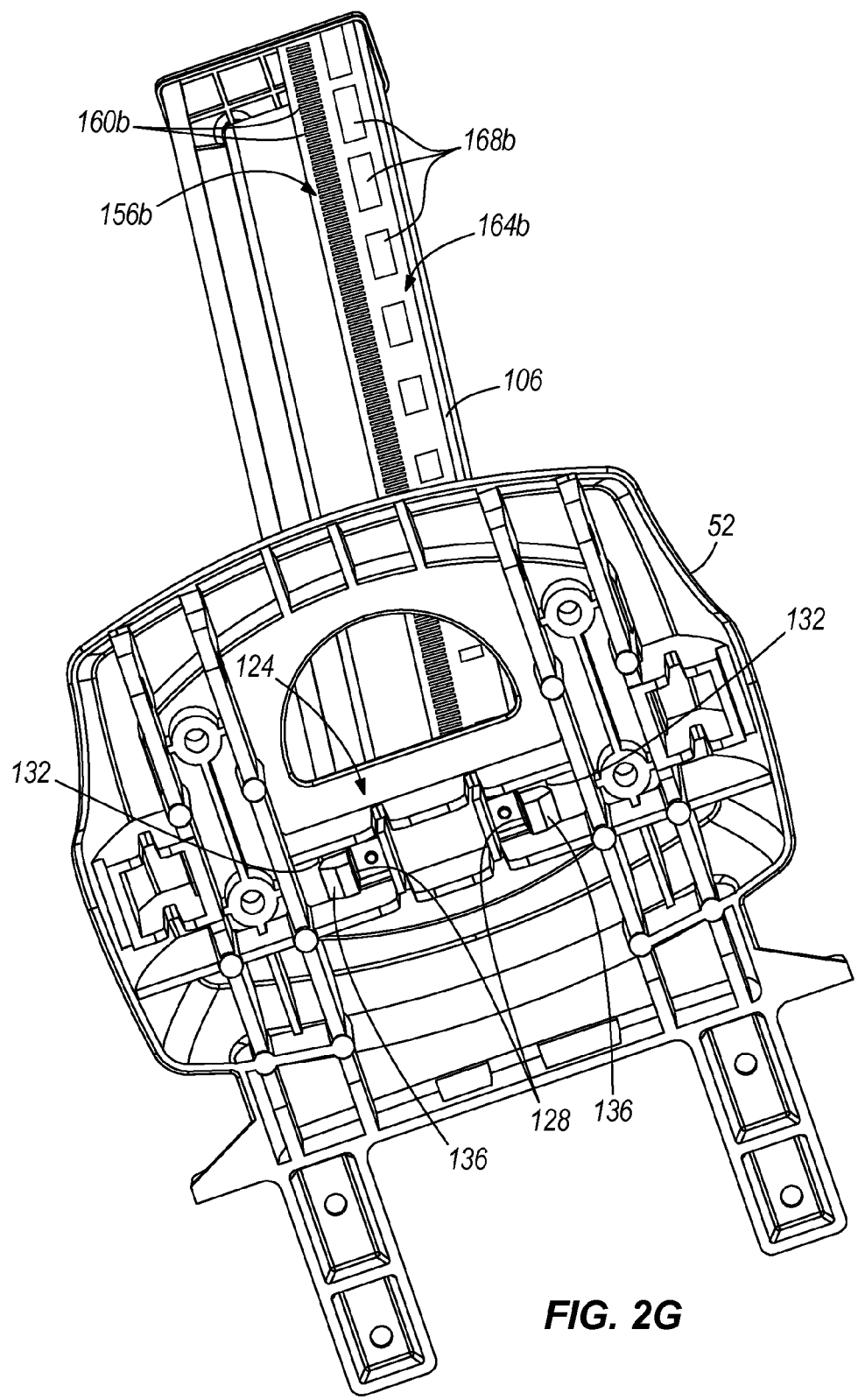

In the retracted positions (e.g., shown in FIG. 2A), to hold the outer rod 106 stationary while the inner rod 102 moves, a locking assembly 124 (see FIG. 2G) is provided between the frame assembly 58 (e.g., the base 52) and the outer rod 106. The locking assembly 124 includes one or more projections or tabs 128 supported on the outer rod 106 and a number of recesses or slots 132 defined in the frame assembly 58 (shown in the base 52). As shown in FIG. 2G, the slots 132 of the locking assembly 124 are defined in the upper wall of the base 52 and are sized to receive at least a portion of the tabs 128.

The illustrated tabs 128 (see FIGS. 2E-2G) generally extend downwardly from the base of the outer rod 106, and each tab 128 includes a projecting end 136. The tabs 128 are resilient (and/or resiliently supported), and, when not positioned in the track 72 of the pillar 56, the projecting ends 136 extend laterally beyond the sides of the outer rod 106 such that the lateral distance between the projecting ends 136 is greater than the width of the outer rod 106 and greater than the lateral distance between the outer edges of the slots 132. The projecting ends 136 are compressed inwardly as the tabs 128 are inserted through the slots 132. Once inserted through the slots 132, the projecting ends 136 move outwardly to lock the outer rod 106 to the base 52 (as shown in FIG. 2G). The locking assembly 124 thus prevents the outer rod 106 from moving with the inner rod 102.

The tabs 128 and the slots 132 are configured such that engagement of the locking assembly is facilitated (e.g., the surfaces of the projecting ends 136 are angled (see FIGS. 2E-2G)). The tabs 128 and the slots 132 are also configured such that disengagement of the locking assembly generally requires the user to apply an unlocking force greater than the force required to slide the inner rod 102 in the track 88 (e.g., the upper surface of each projecting end 136 has a relatively shallow angle (see FIG. 2E)) such that the outer rod 106 is stationary during movement of the inner rod 102.

Figure 2H:
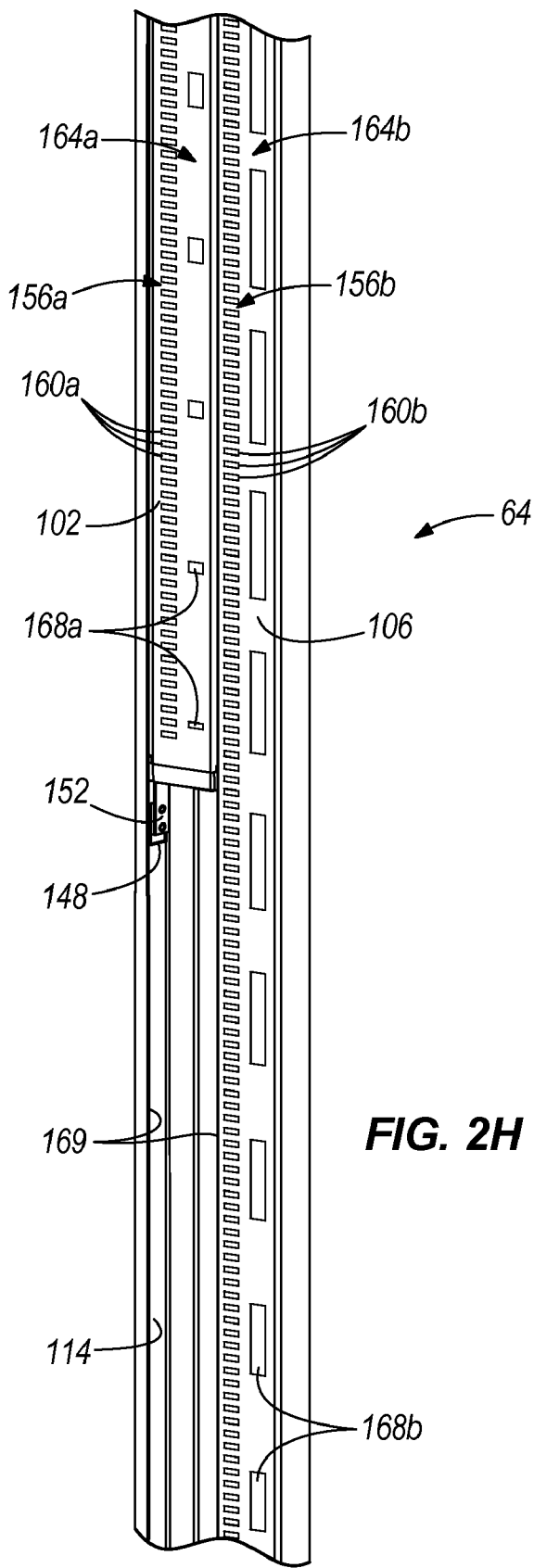
Figure 2I:
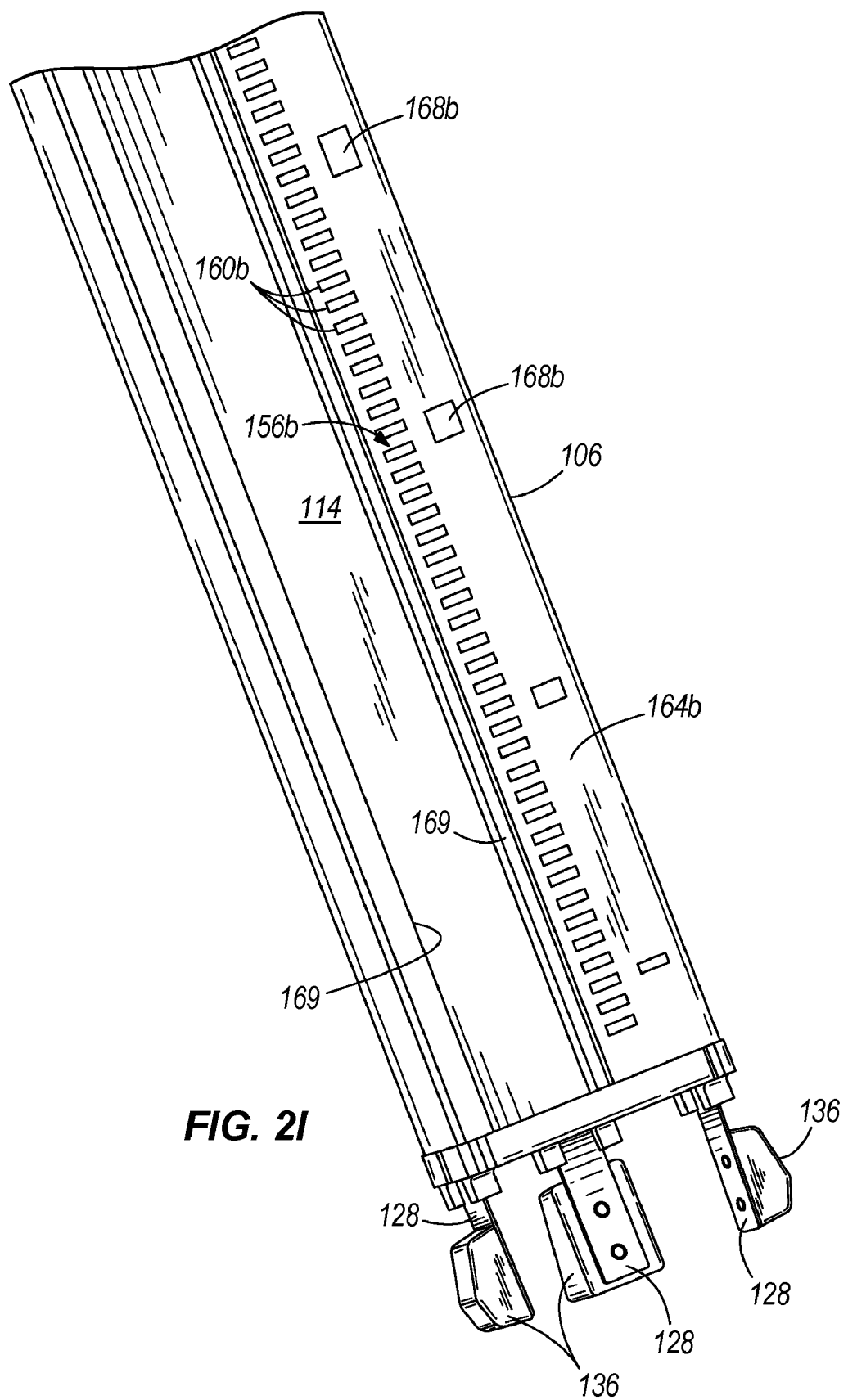

It should be understood that, in other constructions (not shown), the tabs 128 may be supported on the frame assembly 58 (e.g., on the base 52), and the slots 132 may be defined by the outer rod 106. While, in the illustrated construction, two tabs 128 and slots 132 are provided, in other constructions (not shown), one or more than two tabs 128 and slots 132 may be provided. For instance, FIG. 2I depicts an alternate arrangement where the locking assembly 124 includes three tabs 128. In the alternate arrangement of FIG. 2I, the base 52 (not shown in FIG. 2I) includes a third slot 132 to receive the third tab 128. Also, the tab(s) 128 and slot(s) 132 may have a different construction and/or may be located in a different position (e.g., near the top of the rod 106, on the pillar 56, on a different face of the rod 106 (e.g., on the flat face 110 and/or the rounded face)), etc.). In addition, in other constructions (not shown), an actuator may be provided to adjust the locking assembly 124 between the locking condition and the unlocked condition. Furthermore, the slots 132 may be indentations or wells that receive the tabs 128, rather than holes that extend completely through a surface such as the a surface of the base 52.

When the height rod assembly 64 is positioned with the arm 76 approximately even with the top 80 of the pillar 56 (see FIG. 2B), the arm connector 118 has reached and engaged the top 138 of the outer rod 106 (see also FIG. 4). The inner rod 102 and the outer rod 106 include a rod locking assembly 140 such that, when the inner rod 102 and the arm 76 are slid above the top 80 of the pillar 56, the rods 102 and 106 interlock and move up and down together as one integral unit. Movement of the rods 102 and 106 above the top 80 of the pillar 56 also causes the locking assembly 124 to be disengaged such that the outer rod 106 is movable with the inner rod 102 and relative to the frame assembly 58.

The rod locking assembly 140 includes one or more projections or tabs 144 supported on the inner rod 102 and a number of recesses or slots 148 defined by the outer rod 106. As shown in FIG. 2D, the illustrated tabs 144 generally extend downwardly at the base of the inner rod 102, and each tab 144 includes a projecting end 152. The tabs 144 are resilient (and/or resiliently supported), and, when not positioned within the track 88, the projecting ends 152 extend laterally beyond the sides of the inner rod 102 such that the lateral distance between the projecting ends 152 is greater than the width of the inner rod 102 and greater than the width of the track 88. The tabs 144 are compressed so that the projecting ends 152 are moved inwardly towards each other to insert the inner rod 102 within the track 88. When positioned in the track 88 (see, e.g., FIG. 2E), the projecting ends 152 exert an outward force on the inner sidewalls 169 of the track 88.

The slots 148 of the rod locking assembly are defined in the inner side walls 169 of the track 88 and are sized to receive at least a portion of the tabs 144. In the illustrated construction, the slots 148 are defined in a location approximately equal to the length of the inner rod 102 below the top 80 of the pillar 56 along the vertical axis of the track 114 such that, when the arm 76 is at the top 80 of the pillar 56, the projecting ends 152 of the tabs 144 will engage the slots 148. As inner rod 102 is slid upwardly along the track 114, the projecting ends 152 will eventually be aligned with the slots 148, and, when aligned, the projecting ends 152 will move outwardly to engage the slots 148 to lock the inner rod 102 to the outer rod 106. In this locked condition (when the arm 76 is at or above the top 80 of the pillar 56), the inner rod 102 and the outer rod 106 move integrally up and down.

The tabs 144 and the slots 148 are configured such that engagement of the rod locking assembly is facilitated (e.g., the surfaces of the projecting ends 152 are angled). The tabs 144 and the slots 148 are also configured such that disengagement of the rod locking assembly generally requires the user to apply an unlocking force greater than the force required to slide the outer rod 106 in the track 72 (e.g., the lower surface of each projecting end 152 has a shallow angle) such that the inner rod 102 and the outer rod 106 remain movable as a unit and are not inadvertently disengaged.

Figure 2J:
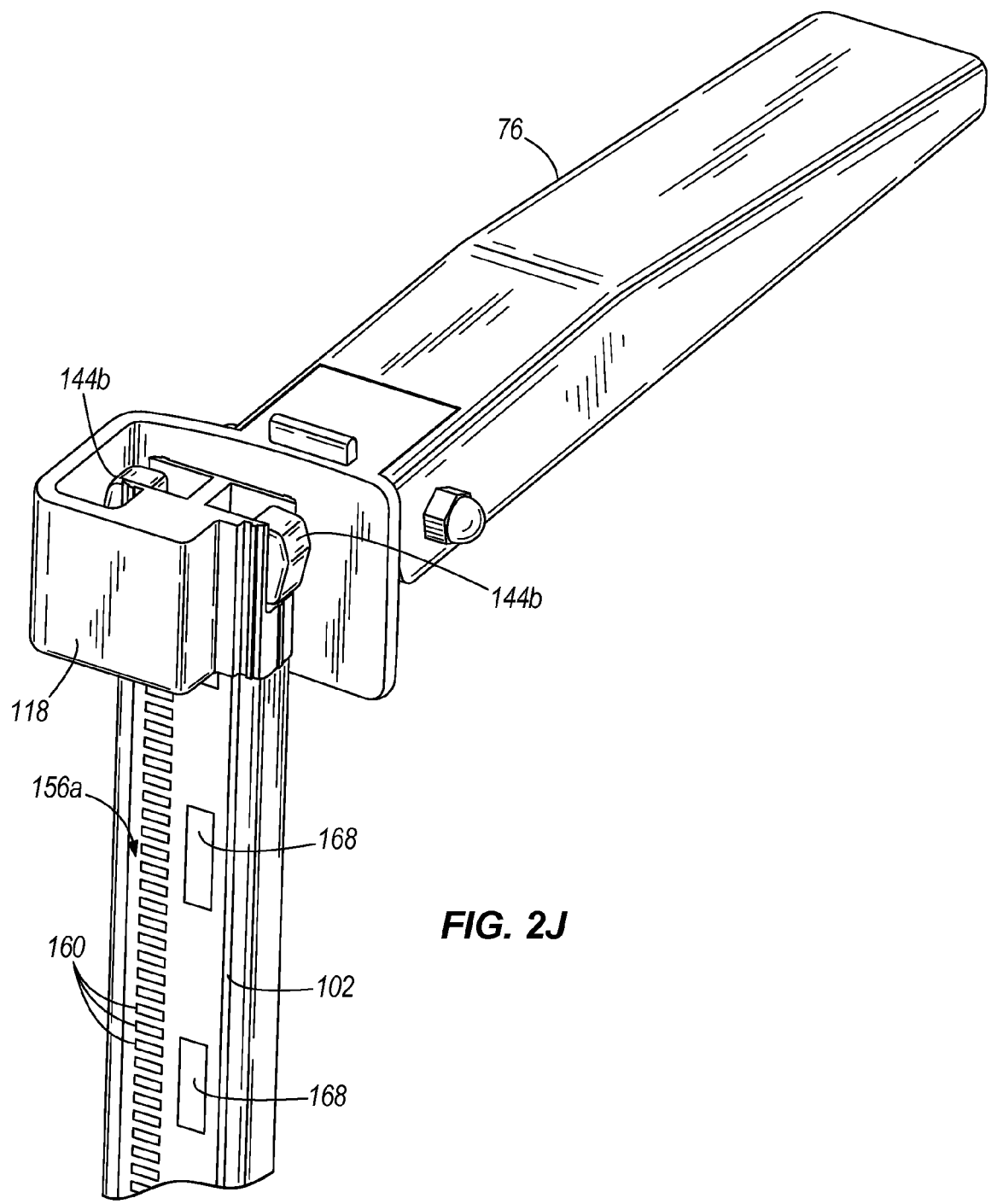

It should be understood that, in other constructions (not shown), the tabs 144 may be supported on the outer rod 106, and the slots 148 may be defined by the inner rod 102. While, in the illustrated construction, two tabs 144 and slots 148 are provided, in other constructions (not shown), one or more than two tabs 144 and slots 148 may be provided. Also, the tab(s) 144 and slot(s) 148 may have a different construction and/or may be located in a different position (e.g., near the top of the rods 102, 106, on a different face of the rods (e.g., on the flat face 110 and/or the rounded face)), etc.). For instance, in FIG. 2J, two tabs 144b are located at the top of the rod 102 near the arm connector 118. These tabs 144b in FIG. 2J may be in addition to or in place of the tabs 144 shown in FIG. 2D. In the arrangement of FIG. 2J, corresponding slots (not shown) are included on the outer rod 106 to receive the tabs 144b. In addition, in other constructions (not shown), an actuator may be provided to adjust the rod locking assembly 140.

In operation, with the arm 76 at or below the top 80 of the pillar 56 (e.g., in FIG. 2A), the locking assembly 124 is engaged (see FIG. 2G) such that the outer rod 106 is held stationary relative to the frame assembly 58 and such that the inner rod 102 is movable relative to the outer rod 106 (and relative to the frame assembly 58). When the arm 76 reaches the top 80 of the pillar 56 (as shown in FIG. 2B), the rod locking assembly 140 is engaged (see FIG. 2H, which depicts projecting end 152 within slot 148), as described above, such that the rods 102 and 106 are movable as a unit.

Further upward movement of the arm 76 (and the rods 102 and 106) above the top 80 of the pillar 56 (e.g., toward the position shown in FIG. 2C) causes the locking assembly 124 to be disengaged such that the outer rod 106 (and the inner rod 102) is movable relative to the frame assembly 58. Upward force is transferred from the arm 76 to the outer rod 106 through the abutment of the arm connector 118 with the top 138 of the outer rod 106 and through the interlocked tabs 144 and slots 148 of the rod locking assembly 140. This upward force is sufficient to cause compression of the projecting ends 136 of the tabs 128 such that the tabs 128 are removed from the slots 132 in the base 52 to unlock the locking assembly 124. Thereafter, as long as the arm 76 remains above the top 80 of the pillar 56, the rods 102 and 106 move integrally relative to the frame assembly 58.

Return movement of the arm 76 (and the rods 102 and 106) to the top 80 of the pillar 56 (see FIG. 2B) causes the locking assembly 124 to be re-engaged, as described above. As the arm 76 is slid down to the top 80 of the pillar 56, the tabs 128 are inserted into the slots 132 of the base 52 (see FIG. 2G) to engage the locking assembly 124 such that the outer rod 106 will be held stationary relative to the frame assembly 58.

Further downward movement of the arm 76 below the top 80 of the pillar 56 (e.g., toward the position shown in FIG. 2A) causes the rod locking assembly 140 to be disengaged such that the inner rod 102 is movable relative to the outer rod 106. The continued downward force on the arm 76 causes the projecting ends 152 to compress so that the tabs 144 disengage the slots 148, unlocking the rod locking assembly 140. Thereafter, as long as the arm 76 remains below the top 80 of the pillar 56, the inner rod 102 is movable up and down the track 114 while the outer rod 106 remains stationary with the locking assembly 124 is in a locked position.

Figure 3:
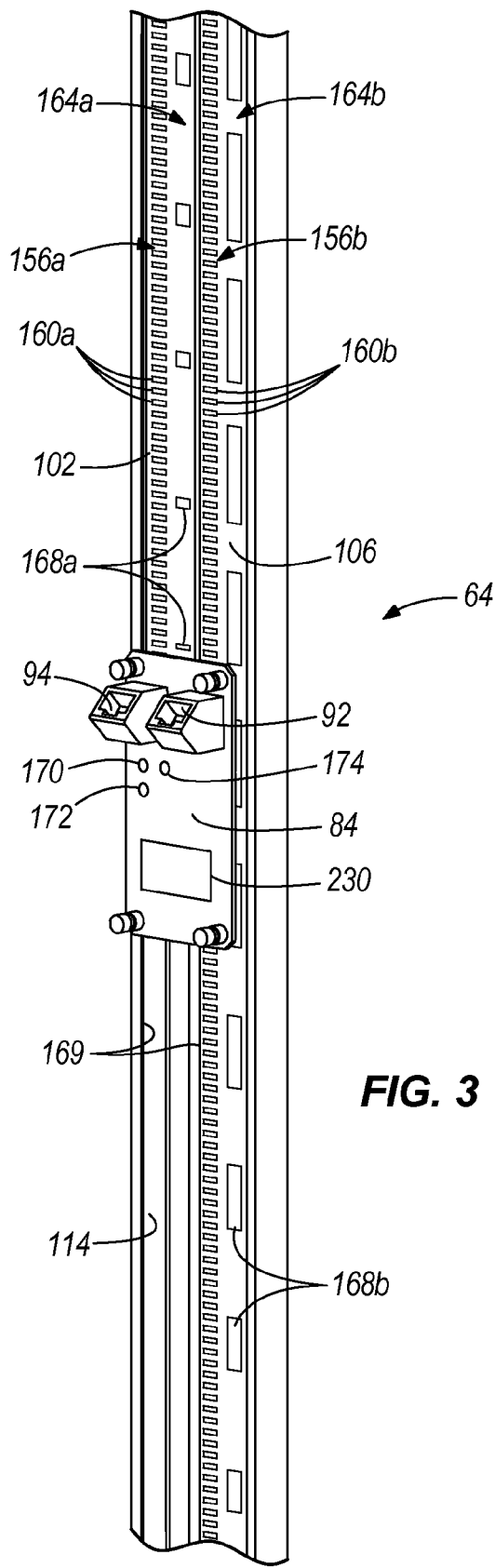
FIG. 3 illustrates a lower sensor board and a portion of the height rod assembly of the scale.

FIG. 3 shows the lower sensor board 84 and the height rod assembly 64 in more detail. The flat face 110 of each rod 102 or 106 includes a number of rows of markings. In the illustrated construction, the rods 102 and 106 respectively include a row 156*a*, 156*b* of uniform markings 160 and a row 164*a*, 164*b* of non-uniform markings 168. Exemplary uniform markings 160 and non-uniform markings 168 are highlighted in FIG. 3.

The lower sensor board 84 includes a number of sensors positioned along the inner rod 102. In particular, two sensors 170 and 172 are positioned over the uniform marking row 156*a*, and one sensor 174 is position over the non-uniform marking row 164*a*. FIG. 4 shows the upper sensor board 86 and height rod assembly 64 in more detail. The upper sensor board 86 includes a number of sensors positioned along the outer rod 106. In particular, two sensors 176 and 178 are positioned over the uniform marking row 156*b*, and one sensor 180 is position over the non-uniform marking row 164*b*.

With the arm 76 below or at the top 80 of the pillar 56 (e.g., FIG. 2A or FIG. 2B), the height of the patient is calculated based the data from sensors 170, 172, 174 of the lower sensor board 84. With the arm 76 above the top 80 of the pillar 56 (when the rod locking assembly 140 is engaged and the arm connector 118 has engaged and lifts the top 138 of the outer rod 106 (e.g., FIG. 2C), the sensors 176, 178, 180 of the upper sensor board 86 provide height information to the controller 98 about the location of the outer rod 106 (and the inner rod 102 which moves with it).

It should be understood that, in other constructions (not shown), the height rod assembly 64 may include a single rod or more than two rods. In such constructions, the sensor arrangement 80 may include a corresponding number of sensor boards. It should also be understood that, in other constructions (not shown), a different sensor arrangement may be provided. In addition, in other constructions (not shown), the rows 156, 164 of markers 160, 168 may be stationary (e.g., on the pillar 56 or another member), while the sensors (e.g., sensors 170, 172, 174 and sensors 176, 178, 180) are secured to and move with the sliding height rod assembly 64.

Figure 5:
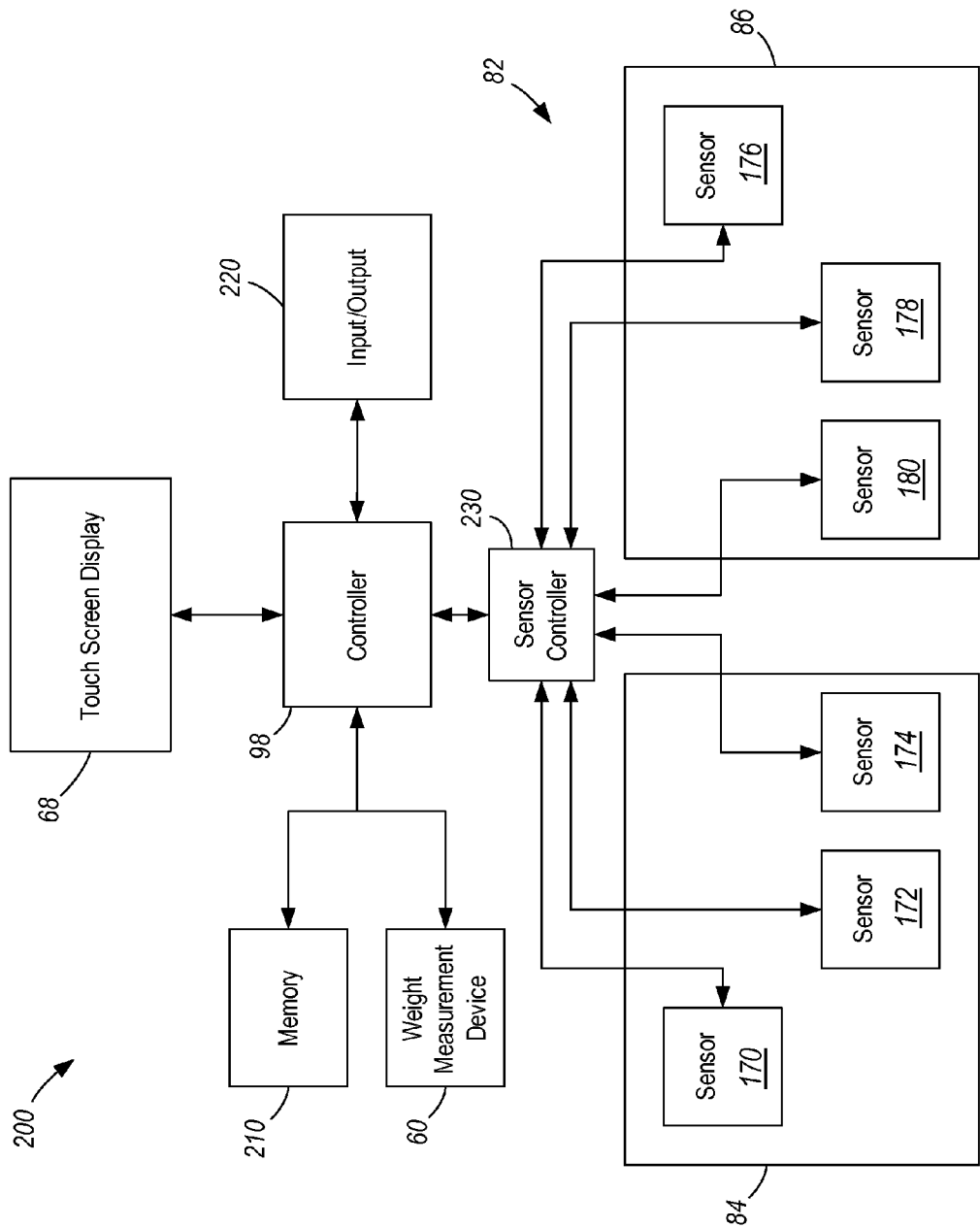
FIG. 5 illustrates a block diagram of a height rod system.

FIG. 5 illustrates a block diagram of the height measurement system 200. The system 200 generally includes the weight measurement device 60, the display 68, the sensor arrangement 82 (the lower sensor board 84 and the upper sensor board 86), the controller 98, a memory 210, an input/output module 220 and a sensor controller 230. Although the block diagram depicts each component as having its own connection to the processor, a shared bus for some or all of the components may be used in some other embodiments.

The display 68 enables a user to enter and review data and select modes of the system 200. For example, the user may enter identifying information such as a name, birth date, etc. of a patient using a displayed virtual keyboard, may navigate the World Wide Web by interacting with a displayed Internet browser, or may interact with other software provided on the system 200 using the display 68. Additionally, the display 68 enables the system 200 to display information to the user. For instance, the display 68 shows the user the current height, weight and/or other data being measured and/or displays data retrieved from the memory 210. In other embodiments, a keyboard, computer mouse, or other computer input device are used to interact with the system 200 (e.g., via the input/output module 220).

The memory 210 provides storage capabilities to the controller 98. Among other data, the memory 210 stores records data and software to be executed by the processor. The records data includes measurements of weight, height, other characteristic(s) as well as data to identify the associated patient or user. The controller 98 is a microcontroller that includes (or is connected to) memory such as memory 210 or other RAM and ROM. The controller 98 executes software that can be stored in the RAM (particularly during execution), the ROM (on a generally permanent basis), or another non-transitory computer readable medium such as other memory or a disc. If necessary, the controller 98 can be connected to such memory or a disc drive to read such software. The controller 98 may be implemented as a microprocessor or other programmable device (e.g., a field programmable gate array (FPGA), an application specific integrated circuit (ASIC), etc.) with suitable memory and I/O devices.

The weight measurement device 60 measures the weight of the patient on the scale 50. The measured weight or a data representation of the weight is transmitted to the controller 98. The sensors 170, 172, 174 and the sensors 176, 178, 180 send data on the position of the inner rod 102 and the outer rod 106, respectively, (e.g., height data) to the sensor controller 230, which relays the height data to the controller 98. The controller 98 uses the height data to determine the positions of the rods 102 and 106 and thereby the height of the subject.

In some embodiments, the controller 98 receives the height and weight measurements and calculates a body mass index ("BMI") of the subject. At least one of the weight, height, BMI, etc. of a subject may be printed by the printer (not shown) and/or shown on the display 68, along with patient identifying information. In other embodiments, other devices are included in the system 200 to measure/determine other characteristic(s), such as, for example, heart rate, blood pressure, time and date of measurement(s), etc.

In some embodiments, the controller 98 stores the height and weight of an individual in memory 210 and uses the stored data to track the height and weight of the individual over time. The controller 98 is operable to compute first and second derivatives to determine the velocity and acceleration of weight loss/gain and the velocity and acceleration of height changes.

The controller 98 also includes predetermined levels of velocity and acceleration. The controller 98 is operable to compare the calculated velocity and acceleration of changes of a characteristic (e.g., weight, height, etc.) against the predetermined levels of velocity and acceleration. The predetermined levels act as thresholds. For example, when a threshold predetermined level for weight is crossed, the tracking module can output an alert or message so that action (e.g., corrective action) can be taken. Predetermined levels are selected, for instance, to ensure that a user's weight loss or gain is within a healthy range. Various other predetermined levels may be used to provide a finer granularity of feedback to a user or a caretaker. A similar calculation and comparison of predetermined levels of acceleration and calculated levels of acceleration can also be performed for other characteristics. Additionally, the messages and alerts, as well as the calculated velocities and accelerations, generated by the controller 98 can be stored in memory 215 and/or shown on the display 68.

As described above, the height rod assembly 64 includes the inner rod 102 and outer rod 106, each with associated sensors (e.g., sensors 170, 172, 174 and sensors 176, 178, 180, respectively). The location of each of the inner rod 102 and the outer rod 106 is detected using a similar methodology, albeit using height data from the respective sensors. Thus, although the location detection is described below with respect to the inner rod 102 and sensors 170, 172, 174, the description also applies to the location detection of the outer rod 106 using sensors 176, 178, 180.

In the illustrated construction, the sensors 170, 172, 174 are optical sensors that output light (e.g., via a light-emitting diode (LED)), detect levels of reflected light, and generate an electrical output accordingly. The level of reflected light received by the optical sensor varies based on whether the sensor is over a white space or a black space. For instance, when the optical sensors 170, 172, 174 receive reflected light off of black or another dark color, the sensors 170, 172, 174 output a logic 1. When the optical sensors 170, 172, 174 detect white space or a light color, the sensors 170, 172, 174 output a logic 0. Of course, in other embodiments, a logic 0 is output for black space, and a logic 1 is output for white space.

A logic value may be represented by an analog output (e.g., +5 V is a logic 1, while 0 V is a logic 0) and interpreted by the sensor controller 230. In some embodiments, the output is proportional the amount of light (or dark) detected. For example, when an optical sensor is over a space that is ⅓ white and ⅔ black, the output will be approximately 70% of the maximum output (e.g., 70%*5 V=3.5 V). The analog output is received by the controller 230. The sensor controller 230 is operable to determine when the analog output is sufficient to be considered a conversion from detecting a white space versus detecting a black space (e.g., the black markings of the inner rod 102). In some embodiments, the cross-over point is 50%. In other embodiments, the cross-over point is slightly more than 50% (e.g., 60%) when converting from a white to a black detection and slightly less than 50% (e.g., 40%) when converting from a black to a white detection.

In some embodiments, the sensor controller 230 controls the sensors 170, 172, 174 to take a reading, which includes outputting light via an LED, detecting the level of reflected light, and generating an output to the sensor controller 230 accordingly. The sensor controller 230 is operable to repeatedly control the sensors 170, 172, 174 to take readings. In some embodiments, when the system 200 is powered (e.g., via a battery source or plugged into a standard wall output power source), the sensors 170, 172, 174 continuously output light via the LED and the sensor controller 230 continuously receives the sensor 170, 172, 174 output (e.g., without needing to proactively poll the sensors 170, 172, 174). In other embodiments, a user input may instruct the sensor controller 230 to control the sensors 170, 172, 174 to take readings for a certain period (e.g., until adjustment of the height rod assembly 64 is completed, until a height measurement is determined, etc.).

The sensor controller 230 is locally coupled on the lower sensor board 84 to the sensors 170, 172, 174. The sensor controller 230 is coupled via connectors 90, 92 to similarly communicate with sensors 176, 178, 180. The sensor controller 230 communicates with the controller 98 via connector 94 and a connector (not shown) on display 68. In some embodiments, the sensor controller 230 functionality is incorporated into the controller 98.

Figure 6B:
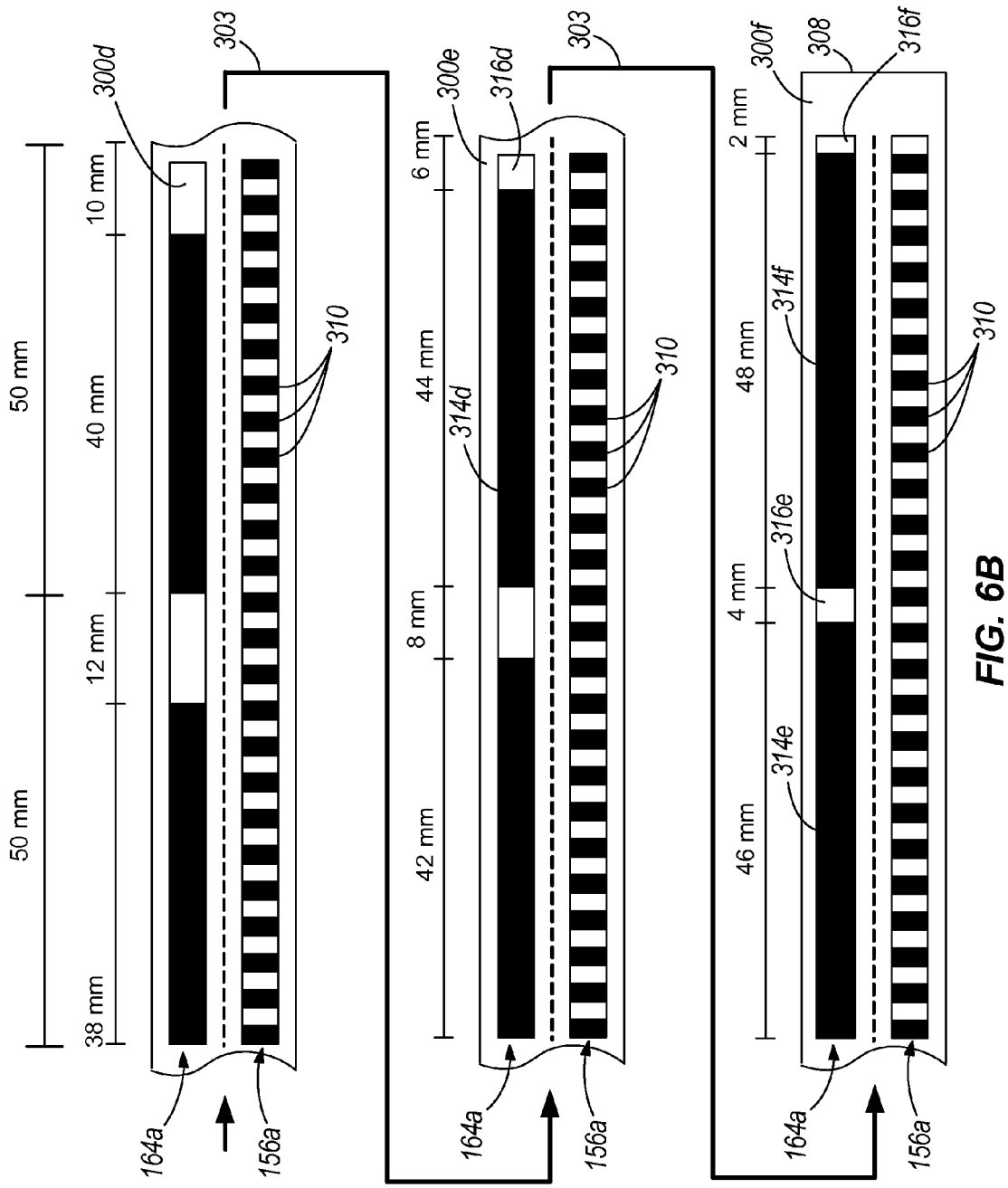

FIGS. 6A-6B depict portions 300a-300f of the inner rod 102. As illustrated in FIGS. 2A-2C, the inner rod 102 is a continuous member. The height rod portions 300a-300c are three continuous sections of a first end 304 of the inner rod 102, and the portions 300d-300f are three sections at the opposite end 308 of the inner rod 102. The arrows 302 illustrate how the portions 300a-300c are connected, and arrows 303 indicate how the portions 300d-300f are connected. Intermediate sections of the inner rod 102 between portions 300c and 300d are not separately illustrated in FIGS. 6A-6B. In some embodiments, the arm 76 is secured to the first end 304 of the inner rod 102.

As mentioned above, the inner rod 102 includes two rows of markings, a uniform row 156a and a non-uniform row 164a. The uniform row 156a includes a plurality of uniform markings 310 (comparable to uniform markings 160 shown in FIGS. 3-4) on one side of the axis 312, with each uniform marking 310 having an equal length along the axis 312 (e.g., 2 mm) and being evenly spaced (e.g., 2 mm) from adjacent uniform markings 310.

The non-uniform row 164a includes non-uniform markings 314 (comparable to non-uniform markings 168 in FIGS. 3-4), each having a unique size (e.g., length along the axis 312). For example, marker 314a is 2 mm long, marker 314b is 4 mm long, marker 314c is 6 mm long, and the length of each marker 314 thereafter (to the right along the inner rod 102) continues to increment by 2 mm. Thus, looking to FIG. 6B, the illustrated final three non-uniform markings 314d, 314e, and 314f have a length of 44 mm, 46 mm, and 48 mm, respectively.

In the illustrated construction, each non-uniform marker 314 resides in an equal length location detection section (e.g., 50 mm) including the non-uniform marking portion 314 and a non-uniform spacing portion 316. In the illustrated example, spacing portion 316a is 48 mm long, spacing portion 316b is 46 mm long, spacing portion 316c is 44 mm long, and the length of each spacing portion 316 thereafter (to the right along the inner rod 102) continues to decrement by 2 mm. Thus, looking to FIG. 6B, the illustrated final three spacing portions 316d, 316e, and 316f have a length of 6 mm, 4 mm, and 2 mm, respectively.

The direction and distance sensors 170, 172 output binary values and, collectively, have a total of four possible states. The direction that the inner rod 102 is moving is determined upon a transition between these states. For instance, if the sensors 170, 172 change from state 1 to state 2, the inner rod 102 is being extended (to the left in FIGS. 6A-6B, up in FIGS. 2A-2C). However, if the sensors 170, 172 change from state 2 to state 1, the inner rod 102 is being retracted (to the right in FIGS. 6A-6B, down in FIGS. 2A-2C). The below table illustrates the four states and the direction of movement of the inner rod 102 that can be inferred based on the transitions between the four states. Additionally, listed in the table are example figures that illustrate each of the four states.

TABLE 1

STATES OF SENSORS 170 AND 172

| States | Sensor 170 (Left) | Sensor 172 (Right) | Direction = Extended Left | Direction = Retracted Right | Example Figures |
|---|---|---|---|---|---|
| State 1 | 1 | 0 | ↓ | ↑ | FIG. 7C |
| State 2 | 0 | 0 | ↓ | ↑ | FIG. 7D |
| State 3 | 0 | 1 | ↓ | ↑ | FIGS. 7E and 7A |
| State 4 | 1 | 1 | ↓ | ↑ | FIG. 7B |
| State 1 | 1 | 0 | ↓ | ↑ | FIG. 7C |
| State 2 | 0 | 0 | ↓ | ↑ | FIG. 7D |
| State 3 | 0 | 1 | ↓ | ↑ | FIGS. 7E and 7A |
| State 4 | 1 | 1 | ↓ | ↑ | FIG. 7B |

FIGS. 7A-7E and FIGS. 8A-8F depict the output of the sensors 170, 172, 174 as the inner rod 102 is extended left and retracted right. For instance, in FIG. 7A, sensors 170 and 174 are not above a marker 310 and, therefore, output a logic 0. The sensor 172, however, is crossing over a marker 310 and, therefore transitions to output a logic 1. Turning to FIG. 7B, as the inner rod 102 continues to be extended, the sensor 172 remains a logic 1 and the sensors 170 and 174 transition to output logic 1 values as the sensors 170, 174 move above a marker 310. Thus, using the table above, as the inner rod 102 moves as depicted in FIG. 7A to FIG. 7B, the sensors 170, 172 transition from state 3 to state 4. Turning to FIGS. 7C-7E, the sensors 170, 172 transition from state 4 to state 1, from state 1 to state 2, and from state 2 to state 3, respectively.

The sensors 170, 172 are also used to determine the distance that the inner rod 102 moves. The controller 98 interprets each state transition as the inner rod 102 having been moved by a given distance (1 mm in the illustrated example). Thus, relative distance traveled and the direction of travel is determined using sensors 170, 172.

Sensor 174, in conjunction with sensors 170, 172, is used to determine the absolute location of the inner rod 102. Since each marker 314 and spacing 316 in the non-uniform row 164*a* is a unique size, the controller 98 determines the location of the inner rod 102 by determining which marker 314 or spacing 316 the sensor 174 is above. To determine which marker 314 the sensor 174 is above, the controller 98 first detects a transition in the output of the sensor 174 (either from a logic 1 to a logic 0 or vice versa). Thereafter, the controller 98 monitors how many uniform markers 310 pass the sensors 170, 172 before another transition of the sensor 174. Once another transition of the sensor 174 output occurs, the total number of uniform markers 310 are summed and multiplied by their size (e.g., 2 mm) to determine the size of the non-uniform marker 314. Once the size of the non-uniform marker 314 is determined, a look up table is accessible or a calculation is performed by the controller 98 to determine the current location of the inner rod 102.

For example, in FIGS. 7A-7E, a transition of the sensor 174 from logic 0 to logic 1 occurs while the short rod is extended starting in FIG. 7B. While the sensor 174 is a logic 1 and the inner rod 102 continues to be extended, sensor 172 transitions once (in FIG. 7C from a logic 1 to a logic 0). Once the sensor 174 output transitions back to a logic 0 in FIG. 7D, the total number of transitions of the sensor 172 is tallied (sensor 170 is used for a similar purpose in other embodiments). The controller 98 multiplies the length of the uniform marker 310 (e.g., 2 mm) by the number of transitions (one) and determines that the sensor 174 is at the first marker 314*a* of the inner rod 102. The controller 98 is then able to use a look up table to determine the height of the arm 76 based on the marker 314*a* of the inner rod 102 being at the sensor 174 (of the lower sensor board 84).

FIGS. 8A-8F depict the 4 mm long marker 314*b* of the inner rod 102 as the marker 314*b* passes by the sensor 174. FIGS. 8A-8F will be described in relation to FIG. 9, which depicts a method 400 of determining the location of a height rod (e.g., inner rod 102) to determine the height of an object.

The method 400 begins in block 402 when the controller 98 is not aware of the location of the inner rod 102. For instance, the controller 98 may generally not be aware of the location of the inner rod 102 upon power-up of the system 200. This situation is a result of the ability to move the inner rod 102 when power is not provided to scale 50 and, therefore, when the controller 98 is not able to monitor such movement.

In step 404, the controller 98 determines whether a state change of at least one of the outputs of the sensors 170, 172, 174 has occurred. The controller 98 repeats step 404 until a transition (or state change) is detected, which is the result of movement of the inner rod 102. In step 406, the controller 98 determines whether the state change included a transition of the output of the sensor 174 from logic 0 to logic 1 or vice versa. If no transition of the output of the sensor 174 is detected, the controller 98 returns to step 404. If a transition of the output of the sensor 174 is detected, the controller 98 proceeds to set a variable X to zero (X=0) in step 408. Additionally, the controller 98 determines the direction of the movement of the inner rod 102 in step 408. The direction is determined based on the state changes of sensors 170, 172 as described above with reference to Table 1.

Thereafter, the controller 98 again monitors for state changes of at least one of the outputs of the sensors 170, 172, 174 in step 410. Upon detection of a state change, the controller 98 determines whether the inner rod 102 is continuing to move in the same direction. If the direction has been changed, the method 400 begins again by returning to step 406 to determine whether the state change detected in step 410 included a change in the output of the sensor 174. If the controller 98 determines that the direction (determined in step 408) has not changed in step 412, the controller 98 proceeds to step 414.

In step 414, the controller 98 determines whether the output of the sensor 172 transitioned from a logic 0 to a logic 1 or vice versa. If so, the controller 98 increments the variable X by 1 (i.e., X=X+1) in step 416. A transition of the output of the sensor 172 indicates that the inner rod 102 has moved 2 mm in the illustrated example.

In step 418, the controller 98 determines whether the state change detected in step 410 included a transition of the output of sensor 174. If a state change did not include a transition of the output of sensor 174, the controller 98 returns to step 410 to await future state changes. However, a transition of the output of the sensor 174 as determined in step 418 indicates that the entire length of one non-uniform marker 314 has passed by the sensor 174. As such, the controller 98 proceeds to step 420 to determine the location of the inner rod 102 based on the determined direction and X value.

In step 420, the controller 98 identifies which non-uniform marker 314 or non-uniform spacing portion 316 traversed the sensor 174. The controller 98 determines whether a non-uniform marker 314 or non-uniform spacing portion 316 traversed the sensor by analyzing the current output of the sensor 174. If the output of the sensor 174 is logic 0, the sensor 174 is currently over non-uniform spacing portion 316, and, therefore, the controller 98 has received data indicating the length of a non-uniform marker 314. If, however, the output of the sensor 174 is logic 1, the sensor 174 is currently over a non-uniform marker 314, and, therefore, the controller 98 has received data indicating the length of non-uniform spacing portion 316.

The controller 98 multiplies the X value by the distance between uniform markers 310 (e.g., by 2 mm). The resulting product indicates the length of the non-uniform marker 314 or non-uniform spacing portion 316, which, as described above, is a uniquely identifying property of each non-uniform marker 314 and non-uniform spacing portion 316. For instance, if X=24, the current output of the sensor 174 is 0, and the distance between uniform markers 310 is 2 mm, the length of a detected non-uniform marker 314 is 48 mm, which indicates that the sensor 174 has sensed non-uniform marker 314*f* (see FIG. 6B). In some embodiments, the value of X is used directly as an input to a look up table to identify the detected marker 314 or spacing 316 or to access and determine the current location of the inner rod 102.

The determined direction is used by the controller 98 to determine which end of the detected non-uniform marker 314 or non-uniform spacing portion 316 that the sensor 174 is located. For instance, if the inner rod 102 is being extended to the left, the controller 98 determines in step 420 that the sensor 174 is located at the right side of a non-uniform marker 314 or non-uniform spacing portion 316 (e.g., the right side of non-uniform marker 314*f*, in the above example).

After step 420, the controller 98 is aware of the location of the inner rod 102. Thus, the controller 98 need only detect future state changes by the sensors 170, 172 (step 422) to update the determined location of the inner rod 102 (step 424). For instance, as described above, each state change of sensors 170, 172 indicates the inner rod 102 has moved 1 mm, and the controller is also able to infer the direction that the inner rod 102 moved.

FIGS. 8A-8F, which depict the inner rod 102 being extended to the left, will now be described in relation to the method 400 of FIG. 9. From FIG. 8A to FIG. 8B, the inner rod 102 is extended to the left, and a state change results, which is detected by the controller 98 in step 404. The state change from FIG. 8A to FIG. 8B includes a transition of the output of the sensor 174, which is detected by the controller 98 in step 406. The controller 98 then sets X to zero and determines that the inner rod 102 is being extended to the left in step 408.

As the inner rod 102 continues to be extended to the left (between FIGS. 8B and 8C) a transition of the output of the sensor 172 is detected in step 410. In response, the controller 98 determines that the inner rod 102 is being extended in the same direction (step 412) and increments the variable X in step 416 (i.e., X=X+1=0+1=1). As the state change resulting between the FIG. 8B and FIG. 8C does not include a transition of the output of the sensor 174 (determined in step 418), the controller 98 returns to step 410. The inner rod 102 continues to be extended to the left between FIGS. 8C and 8D, but the state change does not include a change in the output of the sensor 172 (step 414) or sensor 174 (step 418), and the controller 98 again returns to step 410 via step 418

Figure 8A:
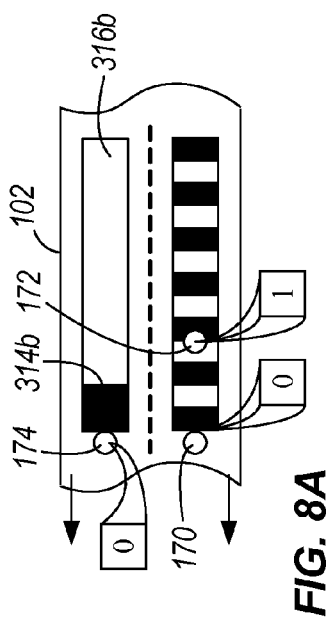
FIGS. 8A-8F illustrate movement of a portion of the height rod assembly relative to sensors and resulting sensor output values
Figure 8B:
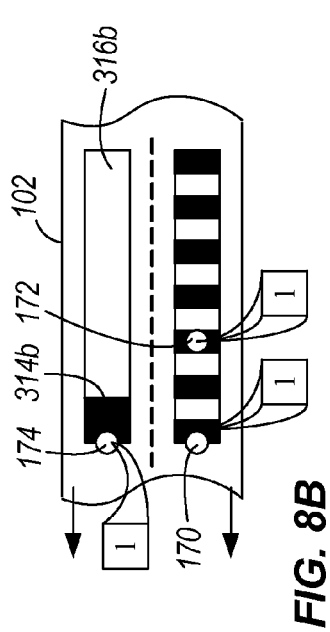
Figure 8C:
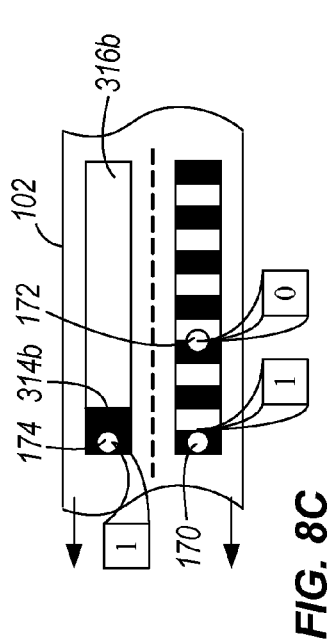
Figure 8D:
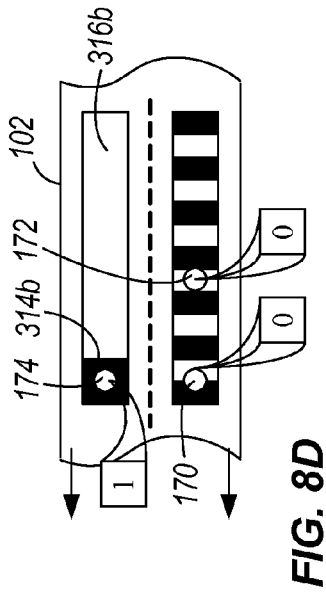
Figure 8E:
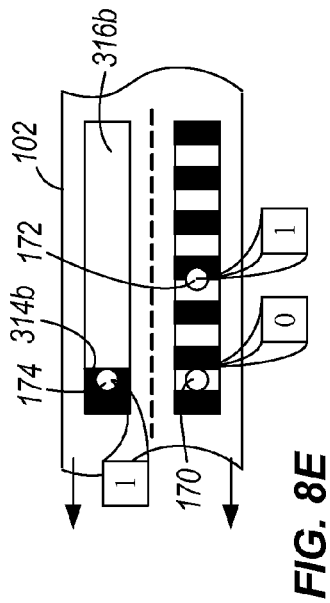
Figure 8F:
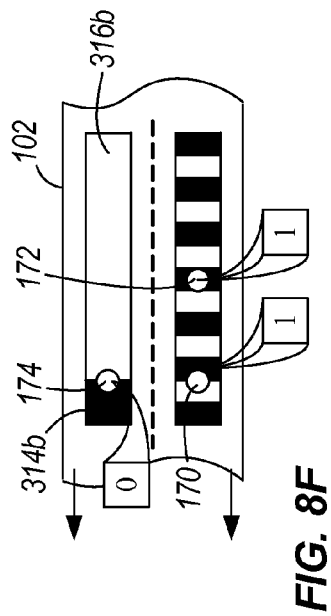
Figure 9A:
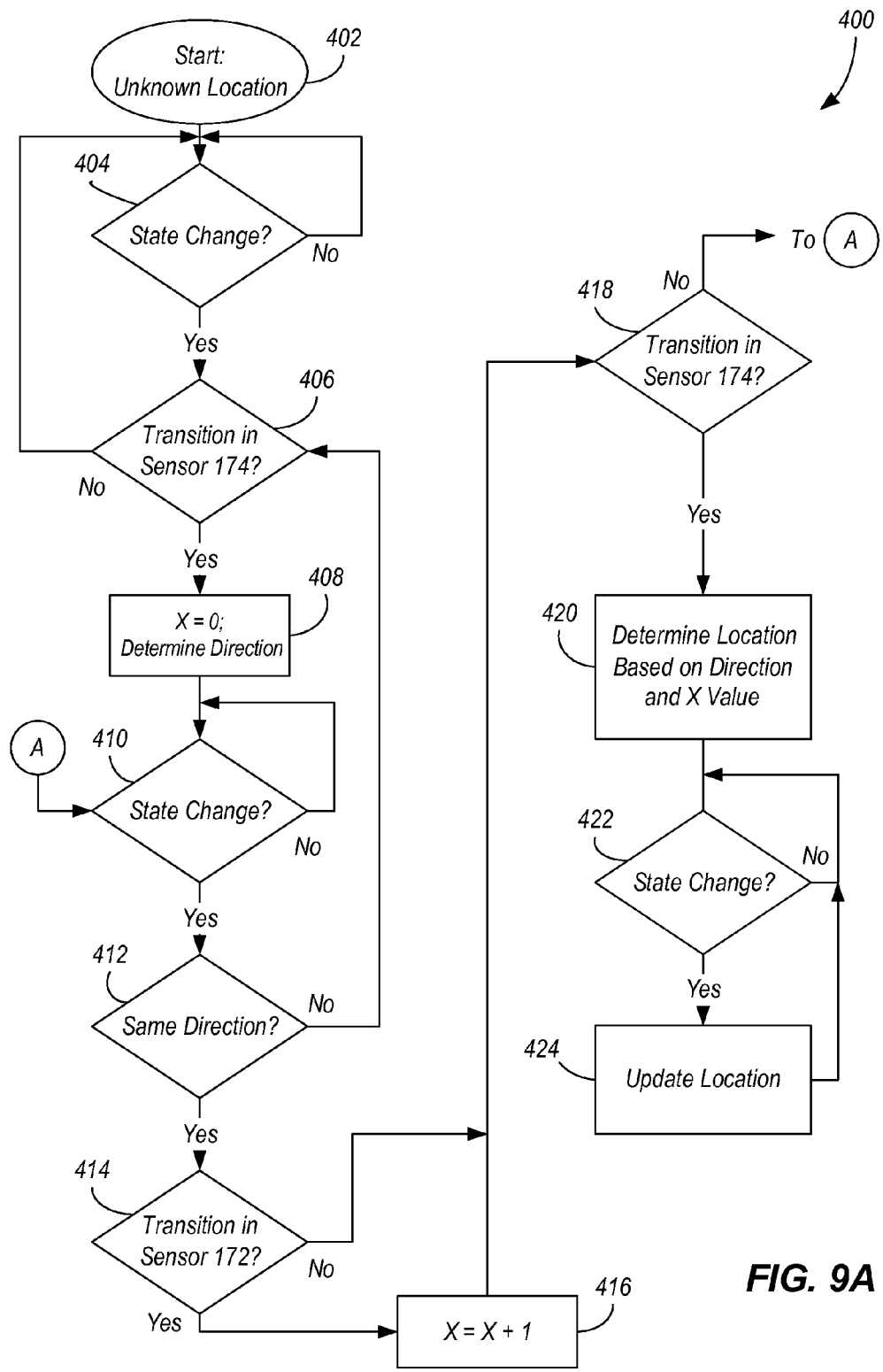
FIGS. 9A-9B illustrate a method of determining the location of a height rod.

The inner rod 102 continues to be extended to the left between FIGS. 8D and 8E, which includes a transition of the output of the sensor 172 (steps 410 to 414). Therefore, the variable X is incremented in step 416 (i.e., X=X+1=1+1=2). The state change resulting between the FIG. 8D and FIG. 8E does not include a transition of the output of the sensor 174 (detected in step 418), and the controller 98 again returns to step 410. The inner rod 102 continues to be extended to the left between FIGS. 8E and 8F, which includes a state change (detected in step 410) with a transition of the output of the sensor 174 (detected in step 418). The controller 98 is aware that an entire non-uniform marker 314 or non-uniform spacing portion 316 has been sensed by the sensor 174, and the location of the inner rod 102 is determined in step 420. In step 420, the current sensor 174 output is logic 0, and, therefore, the controller 98 determines that a non-uniform marker 314 (rather than non-uniform spacing portion 316) traversed the sensor 174. In some embodiments, the determination of whether a non-uniform marker 314 or non-uniform spacing portion 316 is traversing the sensor 174 is made earlier (before step 420) during execution of the method 400.

The controller 98 multiplies the variable X (X=2) by 2 mm to determine that the non-uniform marker 314 has a length of 4 mm. The controller 98 identifies the location of the sensor 174 as being at the right side (because the inner rod 102 is moving left) of the 4 mm long non-uniform marker (i.e., non-uniform marker 314b).

In some embodiments of method 400, instead of returning to step 406 upon detecting a change in direction of the inner rod 102, the variable X is decremented for each uniform marker 310 detected (e.g., in step 414) as the inner rod 102 moves in the opposite direction. Additionally, if the sensor 174 output transitions while the inner rod 102 is moving in the opposite direction, the method returns to step 408.

In some embodiments, the method 400 includes monitoring sensor 170 in step 414 as opposed to sensor 172. Since the sensor 170 and the sensor 174 transition at the same point, the first transition of sensor 170 or the last transition of sensor 170 is not tallied in step 416 for purposes of determining how many uniform markers 310 pass while the sensor 174 is detecting a marker 314 or spacing 316. To effect this alteration, two exemplary changes to the method 400 include the variable X being decremented by one in step 418 or step 408 setting X=−1 (as opposed to 0). Other alterations to method 400 that have similar effects are also possible to enable use of sensor 170 in step 414. Additionally, in some embodiments, the method 400 increments X by 1 in step 416 for each state change detected in step 410. Then, in step 420, X is not multiplied by two as it already represents the number of mm by which the inner rod 102 has moved. Similar to monitoring sensor 170, however, X must be decremented by one in step 418 or a similar step occurs to ensure proper distance calculations.

Regardless, in the illustrated construction, the method 400 results in a determination of the location of the height rod assembly 64 by moving the height rod assembly 64 by 52 mm at most. Thus, the location of the arm 76 is known quickly without having to move the height rod assembly 64 long distances.

Figure 9B:
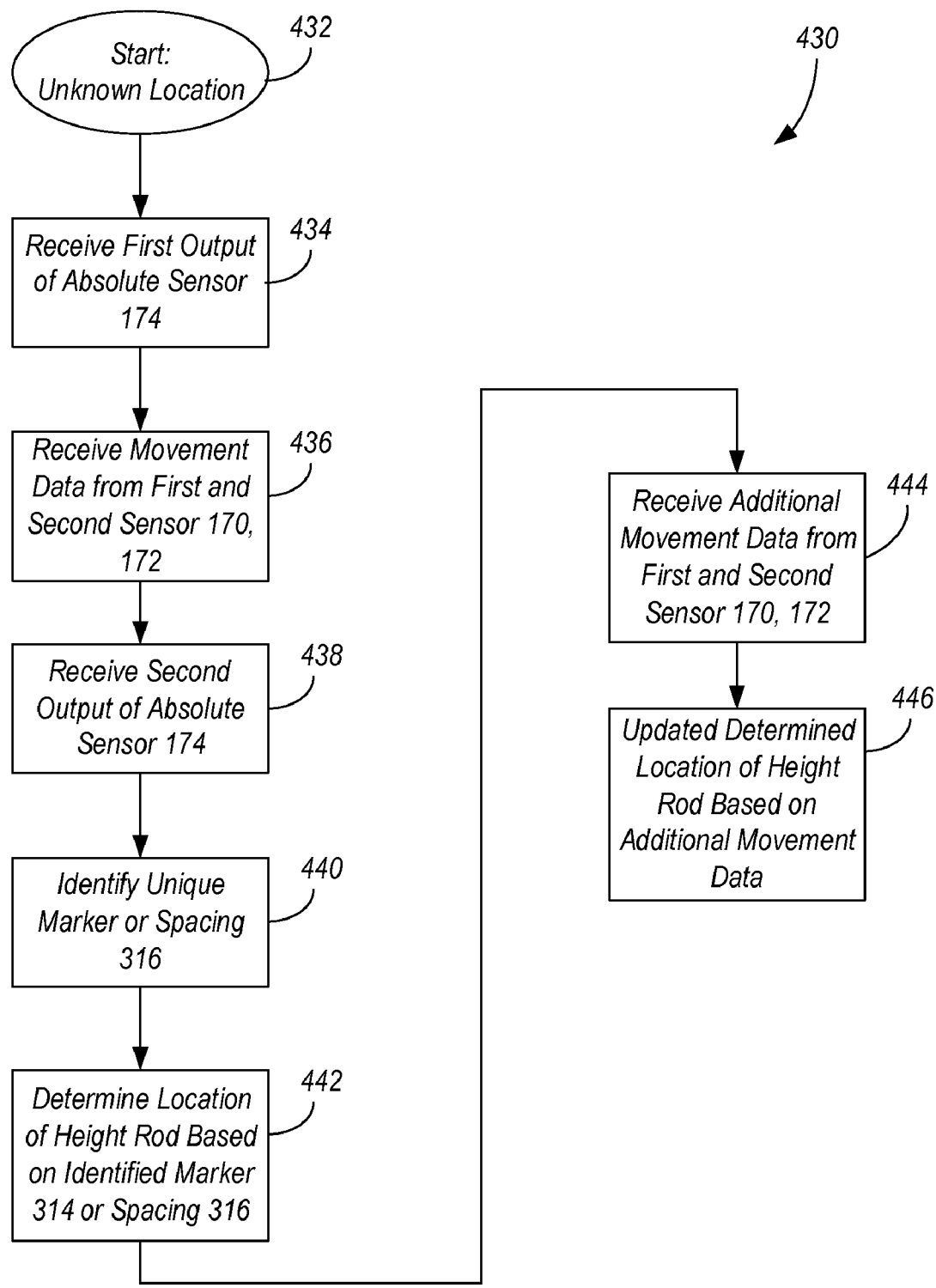

FIG. 9B depicts method 430, which is another illustration of method 400. That is, the steps of method 430 correlate to steps described with respect to method 400. Similar to method 400, the method 430 begins with the location of the height rod assembly 64 being unknown (step 432). In step 434, a controller 98 receives a first output from an absolute sensor (e.g., sensor 174 or 180) indicating a transition. Step 434 correlates to steps 404 and 408 of method 400. In step 436, the controller 98 receives movement data from a first and second sensor (e.g., sensors 170, 172 or sensors 176, 178). The movement data indicates a direction and distance of movement of the inner rod 102 since the transition of the sensor 174 in step 434. Step 436 correlates to steps 410, 412 and 414 of method 400. In step 438, the controller 98 receives a second output from the absolute sensor indicating a second transition. Step 438 correlates to step 418 of method 400. In step 440, the controller 98 identifies the non-uniform marker 314 or spacing portion 316 that passed by the absolute sensor 174 or 180 using the movement data occurring between the transitions of steps 434 and 438. In step 442, the location of the height rod assembly 64 is determined based on the identified non-uniform marker 314 or spacing portion 316. Steps 440 and 442 correlate to step 420 of method 400. Thereafter, additional movement data is received by the controller 98 from the first and second sensor 170, 172 or 176, 178 in step 444. In step 446, the controller 98 updates the determined location of the height rod assembly 64 based on the additional movement data. Steps 444 and 446 correlate to steps 422 and 424 of the method 400, respectively.

In some embodiments, an additional sensor 448 is provided that functions similar to sensor 174 (and sensor 180) in determining the absolute location of the height rod assembly 64. To modify method 400 for use with the sensor 448, step 406 and step 418 are modified. Step 406 is modified such that a transition of either of sensor 174 or sensor 448 causes the controller 98 to proceed to step 408. Step 418 is modified such that only the sensor that had its output transition in step 406 is monitored in step 418 (e.g., sensor 174 or sensor 448, but not both). Slight alterations to the method may be necessary depending on the specific location of sensor 448 relative to the sensors 170, 172. For instance, the method 400 would not need additional alterations if the sensor 448 is placed so that it transitions at the same instant as sensor 170, similar to sensor 174. However, if the sensor 448 transitions at the same instant as sensor 172, the controller 98 monitors transitions of sensor 170 instead of sensor 172 in step 414, the variable X is decremented by one in step 408 or 418, or a similar adjustment is made.

Figure 10:
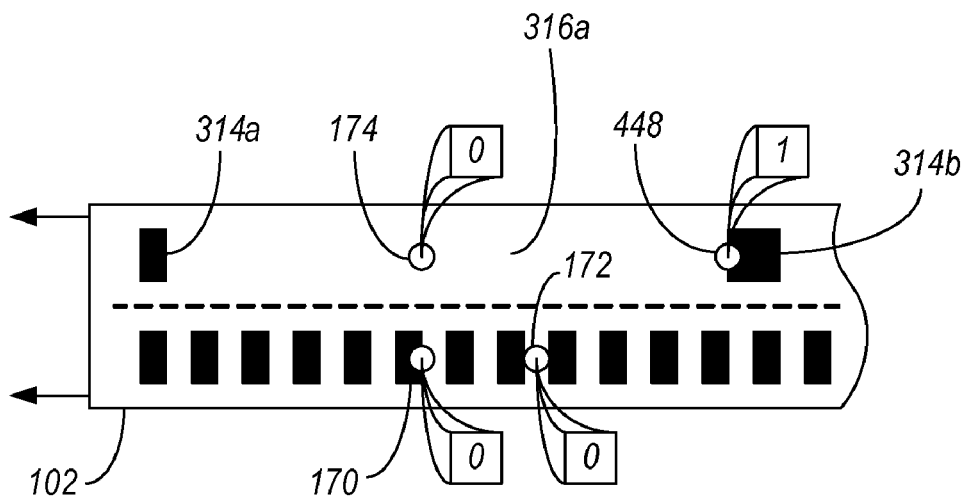
FIG. 10 illustrates an alternative sensor arrangement.

In the embodiment depicted in FIG. 10, the controller 98 is operable to detect the location of the inner rod 102 within a reduced distance. Placement of additional sensors similar to sensors 174 and 448 will further reduce the distance that the inner rod 102 needs to travel before its location is determined. Furthermore, placement of the additional sensor 448 at a different distance relative to the sensor 174 (e.g., 10 mm, 20 mm, 30 mm, 40 mm, etc.) would have a similar effect.

In some embodiments, the distance that the height rod assembly 64 needs to travel to determine the location of the height rod assembly 64 is further reduced by decreasing the length of the uniform and non-uniform markers 310 and 314 and the space between each. With more accurate optical sensors, relatively shorter length markers 310, 314 and spaces between the markers 310 and 314 are usable, resulting in a shorter distance that the height rod assembly 64 needs to move to determine the location of the height rod assembly 64.

Figure 11:
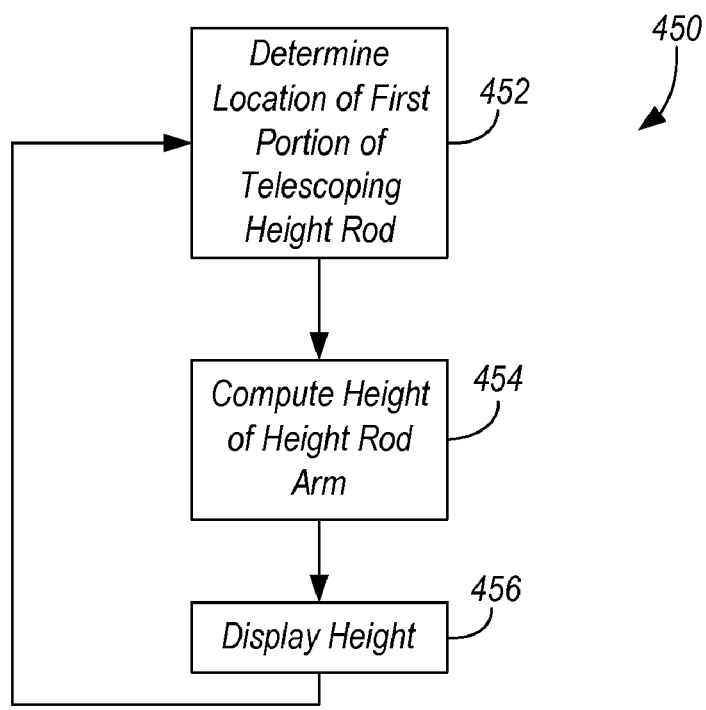
FIG. 11 illustrates a method of determining the height of an object using a height rod device.

FIG. 11 depicts a method 450 to determine the height of an object using a digital height rod system (e.g., digital height rod system 200). The method 450 is capable of determining the height of an object using a single-piece height rod or a multi-piece, telescoping height rod (e.g., height rod assembly 64). In step 452, the location of the height rod assembly 64 is determined. For instance, the method 400 is used to determine the location of inner rod 102 or outer rod 106, depending on which is moved, such that the location of the rod 102 or 106 is detected. In particular, step 452 is completed upon reaching step 420 or step 424 of method 400.

Once the location of the height rod is determined, the controller 98 proceeds to step 454 to compute the overall height of the arm 76 of the height rod assembly 64. If the inner rod 102 is in a low position (e.g., as depicted in FIG. 2A), the sensors 170, 172, 174 are used to determine the height of the arm 76. In these situations, the outer rod 106 has not yet been engaged and lifted by the arm connector 118.

For instance, if the controller 98 determines that that the inner rod 102 is at position 455 (see, e.g., FIG. 6A), which is at a uniform marker 310 that is 12 mm below (to the right) of the non-uniform marker 314c, the controller 98 computes that the arm 76 is 118 mm above the sensor 174 (assuming the arm 76 is attached to the first end 304 of the inner rod 102). The distance 118 mm is calculated as follows: distance=118 mm=50 mm (length between left-most point of markers 314a and 314b)+50 mm (length between left-most point of markers 314b and 314c)+6 mm (length of marker 314c)+12 mm (three uniform markers 310 to the right of the marker 314c and the space therebetween). The height of the sensor 174 (e.g., from the top surface of the base 52) is a known value (e.g., X mm) and is added to the distance that the arm 76 is above the sensor 174 (e.g., 118 mm) to reach a final height (e.g., X mm+118 mm).

In step 456, the computed height is displayed on the display 68 of display 68. The controller 98 is operable to repeat the method 450 and return to step 452. Thus, as the height rod assembly 64 and arm 76 slide up and down, the height displayed is continuously updated on the display 68.

In situations in which the outer rod 106 has been engaged by the arm connector 118 (and the rod locking assembly 140 is engaged) and the arm 76 is in an extended position (see, e.g., FIG. 2C), the inner rod 102 and markings 160a, 168a are no longer in front of the sensors 170, 172, 174. As such, the sensors 176, 178, 180 of the upper sensor board 86 are used to determine the particular location of the arm 76. In step 454, the distance between the arm 76 and the sensor 180 is calculated in a manner similar to how the distance between the arm 76 and the sensor 174 is calculated. Thereafter, this distance value is added to the height of the sensor 180 (e.g., from the top surface of the base 52), which is a known value (e.g., Y mm), to reach a final height.

In some embodiments, the total height calculation is computed using a different order of operations or different offset values (e.g., based on the location of sensor 172 instead of sensor 174) to reach the same final height of the object.

In some embodiments, the digital height rod system 200 (including the height rod assembly 64 with arm 76) are mounted to a wall, as opposed to being a free-standing system coupled to a base 52. In these embodiments, the distances between the arm 76 and the sensors 174, 180 are computed similarly, but the offset of height of the sensor 174 or sensor 180 may be different. In some embodiments, the heights of the sensor 174 and sensor 180 for a wall mount set-up are entered into the controller 98 via display 68.

Figure 12:
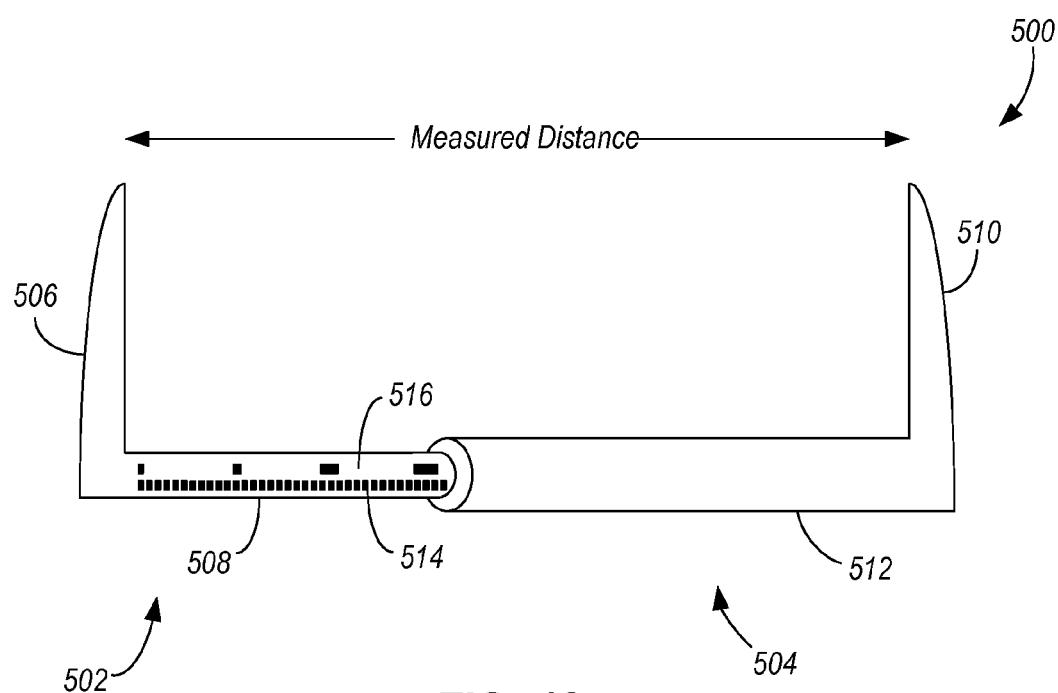
FIG. 12 illustrates an alternative construction of a measuring device.

In other embodiments, the digital height rod system 200 is intended for measuring objects on a flat generally horizontal surface (e.g., an infant, animal, or other object on a table; see, for example, FIG. 12, which includes a digital height rod 500 including a first portion 502 and a second portion 504). The first portion 502 includes an arm portion 506 and an insertion portion 508, and the second portion includes an arm portion 510 and a receiving portion 512 for receiving the insertion portion 508. The first portion 502 and second portion 504 have a telescoping arrangement to adjust the distance between the arms 506 and 510.

The distance between the arms 506 and 510 is measured by a system and method similar to that described above. For example, one of the first portion 502 and second portion 504 includes a non-uniform marking row and a uniform marking row, and a sensor board with three sensors (not shown, but similar to sensors 170, 172, 174) are positioned to read the markings. The determination of which marking or spacing the sensor board is currently reading is interpreted to provide a distance value. In FIG. 12, the insertion portion 508 includes marking rows 514 and 516, and the receiving portion 512 has a sensor board mounted thereon to sense the markings and spacings.

In some embodiments (not shown), markings and spacing portions having a shape different than the illustrated rectangles may be used in the height rod assembly 64 (to replace and/or supplement the illustrated rectangular markings/spacing portions). In some embodiments, the optical sensors output values representing more than two states (e.g., more than logic 0 and 1). For instance, the output of a single optical sensor may represent any of three or four states depending on the level of analog signal output. With additional states, two non-uniform sensor markings with a different shape or level of shading, but having the same length, are able to be distinguished by the optical sensors.

In some embodiments (not shown), the non-uniform markings and spacing portions may be replaced and/or supplemented with one or more unique encoded patterns (e.g., similar to a bar code). The optical sensors are thus able to detect the absolute location of the height rod assembly 64 by determining which encoded pattern is being read. In still further embodiments, the uniform and non-uniform markers may be replaced and/or supplemented with mechanical markers (e.g., grooves), and the optical sensors may be replaced and/or supplemented with mechanical sensors that detect the grooves and output an analog value in response to a detected groove.

One or more independent features and advantages of the invention may be set forth in the following claims.

What is claimed is:

1. A device for measuring the length of an object, the device comprising:
- a first member;
- a second member movable relative to the first member;
- a uniform marking row including uniform markers, each uniform marker having a first length;
- a non-uniform marking row divided into equal sections, each section including a unique marker and a unique spacing, a length of the unique marker and a length of the unique spacing of each section each uniquely identifying the section;
- a first sensor positioned to detect the uniform markers as the first member and the second member are relatively moved, the first sensor generating a first output indicative of whether a uniform marker is detected;
- a second sensor positioned to detect the uniform markers as the first member and the second member are relatively moved, the second sensor generating a second output indicative of whether a uniform marker is detected;
- an absolute sensor positioned to detect the unique markers and unique spacings as the first member and the second member are relatively moved, the absolute sensor generating an absolute output, the absolute output indicating transitions between the unique markers and unique spacings; and
- a controller coupled to the first sensor, the second sensor, and the absolute sensor, the controller determining a location of the movable member based the first output, the second output, and the absolute output to thereby determine the length of the object.

2. The device of claim 1, further comprising a digital display coupled to the controller, the controller outputting a determined length of the object to the digital display, the digital display displaying the determined length.

3. The device of claim 1, wherein the controller determines a direction of relative movement of the first member and the second member based on the first output and second output.

4. The device of claim 1, wherein the controller determines an initial location of the first member relative to the second member based on the absolute output.

5. The device of claim 4, wherein the controller determines an updated location based on the initial location and based on transitions of the first output and the second output occurring after the determination of the initial location.

6. The device of claim 1, wherein the controller determines an initial location of the height rod by identifying one of a first unique marker of the unique markers and a first unique spacing of the unique spacings.

7. The device of claim 1, further comprising a second absolute sensor positioned to detect the unique markers and unique spacings and generate a second absolute output to the controller.

8. The device of claim 1, wherein the second sensor is offset from the first sensor in a direction of travel of the uniform marking row such that the first output and the second output transition at different times.

9. The device of claim 1, wherein the second member includes a frame, and wherein the first member includes a height rod movable relative to the frame.

10. The device of claim 1, wherein the first member includes a first rod and a second rod forming a telescoping rod assembly, the first rod having the first-mentioned uniform marking row and the first-mentioned non-uniform marking row, the second rod having a second uniform marking row including second uniform markers, and a second non-uniform marking row divided into equal sections, each section including a unique marker and a unique spacing, a length of the unique marker and a length of the unique spacing of each section each uniquely identifying the section of the second non-uniform marking row; wherein the device further comprises:
- a third sensor positioned to detect the second uniform markers as the second rod is moved, the third sensor generating a third output indicative of whether a second uniform marker is detected;
- a fourth sensor positioned to detect the second uniform markers as the second rod is moved, the fourth sensor generating a fourth output indicative of whether a second uniform marker is detected; and
- a second absolute sensor positioned to detect the unique markers and unique spacings of the second non-uniform marking row, the second absolute sensor generating a second absolute output indicating transitions between the unique markers and unique spacings of the second non-uniform marking row; and
- wherein the controller is coupled to the third sensor, the fourth sensor, and the second absolute sensor and determines a location of the second rod based the third output, the fourth output, and the second absolute output.

11. The device of claim 9, further comprising a locking assembly operable to lock the first rod in a position relative to the second rod.

12. The device of claim 9, further comprising a scale assembly supported by the frame and operable to determine a weight of the object.

13. A device for detecting a length of an object along an axis, the device comprising:
- a telescoping rod assembly including a first rod and a second rod extendable along the axis;
- a first sensor board operable to detect markings on the first rod and output first length data;
- a second sensor board operable to detect markings on the second rod and output second length data, the second sensor board being spaced from the first sensor board along the axis; and
- a controller coupled to the first sensor board and to the second sensor board, the controller being operable to
  - receive the first length data and the second length data,
  - determine the length of the object using the first length data when the telescoping rod assembly is positioned below a predetermined level, and
  - determine the length of the object using the second length data when the telescoping rod assembly is positioned above the predetermined level.

14. The device of claim 13, wherein the first sensor board includes a first relative sensor, a second relative sensor, and a first absolute sensor, and wherein the second sensor board includes a third relative sensor, a fourth relative sensor, and a second absolute sensor.

15. The device of claim 14, wherein the first relative sensor and the second relative sensor encode a distance and a direction of movement of the first rod.

16. The device of claim 13, wherein the controller determines the length of the object independent of the second length data when the telescoping rod is positioned below the predetermine level and determines the length of the object independent of the first length data when the telescoping rod assembly is positioned above the predetermine level.

17. The device of claim 13, further comprising an intermediate controller coupled to
- the first sensor board to receive the first length data,
- the second sensor board to receive the second length data, and the controller to forward the first length data and second length data to the controller.

18. The device of claim 13, wherein the first rod moves independently of the second rod when the telescoping rod assembly is positioned below the predetermined level.

19. The device of claim 13, further comprising a locking assembly operable to lock the first rod to the second rod for integral movement when the telescoping rod assembly is positioned above the predetermined level.

20. The device of claim 19, wherein the locking assembly includes a projection supported by one of the first rod and the second rod and a recess defined by the other of the first rod and the second rod, the projection being selectively engageable in the recess to lock the first rod to the second rod.

21. The device of claim 19, further comprising:
a frame operable to movably support the telescoping rod assembly; and
a second locking assembly operable to lock one of the first rod and the second rod to the frame during movement of the other of the first rod and the second rod relative to the frame.

22. The device of claim 13, further comprising:
a base supportable on a surface;
a pillar for housing tracks on which the first rod and the second rod move, and
a display head supported on the pillar and operable to display a determined length of the object; and
wherein the predetermined level is at a top of the pillar.

23. A method for determining a length of an object, the method comprising:
moving a first member relative to a second member;
receiving a first output from an absolute sensor indicating that the absolute sensor has transitioned between a marker and a spacing of a non-uniform marking row, the non-uniform marking row being divided into equal sections, each section including a unique marker and a unique spacing, a length of the unique marker and a length of the unique spacing of each section uniquely identifying the section;
receiving movement data from a first sensor and a second sensor indicating a direction and distance of relative movement of the first member and the second member since the transition of the absolute sensor;
receiving a second output from the absolute sensor indicating a subsequent transition of the absolute sensor from one of the marker and the spacing to one of a second spacing and a second marker;
identifying one of the marker and the spacing based on the first output, the second output, and the movement data; and
determining a location of the first member relative to the second member based on the identification of one of the marker and the spacing.

24. The method of claim 23, further comprising:
receiving additional movement data from the first sensor and the second sensor indicating a direction and distance of further relative movement of the first member and the second member;
updating the determined location of the first member relative to the second member based on the additional movement data.

25. The method of claim 23, wherein the movement data received between the first output and the second output indicates the length of one of the marker and the spacing enabling identification of one of the marker and the spacing.

* * * * *